US008353297B2

(12) United States Patent
Dacquay et al.

(10) Patent No.: US 8,353,297 B2
(45) Date of Patent: Jan. 15, 2013

(54) PULSE MANIPULATION FOR CONTROLLING A PHACOEMULSIFICATION SURGICAL SYSTEM

(75) Inventors: Bruno Dacquay, Irvine, CA (US); Douglas M. Fanney, San Clemente, CA (US); Mikhail Boukhny, Laguna Beach, CA (US)

(73) Assignee: Novartis AG, Basel (CH)

( * ) Notice: Subject to any disclaimer, the term of this patent is extended or adjusted under 35 U.S.C. 154(b) by 1703 days.

(21) Appl. No.: 11/215,923

(22) Filed: Aug. 31, 2005

(65) Prior Publication Data

US 2007/0073214 A1  Mar. 29, 2007

(51) Int. Cl.
*A61B 19/00* (2006.01)

(52) U.S. Cl. .............. 128/898; 604/22; 623/6.11; 601/2

(58) Field of Classification Search .................. 606/4–6, 606/107; 604/22; 623/6.11–6.13; 601/1, 601/2; 607/72
See application file for complete search history.

(56) References Cited

U.S. PATENT DOCUMENTS

| 3,589,363 A | 6/1971 | Banko et al. |
| 3,941,122 A | 3/1976 | Jones |
| 4,223,676 A | 9/1980 | Wuchinich et al. |
| 4,246,902 A | 1/1981 | Martinez |
| 4,493,694 A | 1/1985 | Wuchinich |
| 4,515,583 A | 5/1985 | Sorich |
| 4,589,415 A | 5/1986 | Haaga |
| 4,609,368 A | 9/1986 | Dotson, Jr. |
| 4,827,911 A | 5/1989 | Broadwin et al. |
| 4,869,715 A | 9/1989 | Sherburne |
| 4,922,902 A | 5/1990 | Wuchinich et al. |
| 4,989,583 A | 2/1991 | Hood |
| 5,090,425 A * | 2/1992 | Stahl ............................ 128/898 |
| 5,154,694 A | 10/1992 | Kelman |
| 5,359,996 A | 11/1994 | Hood |
| 6,175,180 B1 | 1/2001 | Angelini et al. |
| 6,179,808 B1 | 1/2001 | Boukhny et al. |
| 6,261,283 B1 | 7/2001 | Morgan et al. |
| 6,261,297 B1 | 7/2001 | Kadziauskas et al. |
| 6,319,220 B1 | 11/2001 | Bylsma |
| 6,402,769 B1 | 6/2002 | Boukhny |
| 6,629,948 B2 | 10/2003 | Rockley et al. |
| 7,077,820 B1 * | 7/2006 | Kadziauskas et al. ......... 604/22 |
| 7,363,088 B2 * | 4/2008 | Han et al. ....................... 607/74 |
| 2002/0082793 A1 | 6/2002 | Kadziauskas et al. |
| 2004/0092921 A1 * | 5/2004 | Kadziauskas et al. ......... 606/27 |
| 2004/0092922 A1 | 5/2004 | Kadziauskas et al. |
| 2006/0195077 A1 * | 8/2006 | Kadziauskas et al. .......... 606/4 |
| 2007/0078379 A1 * | 4/2007 | Boukhny et al. ............... 604/27 |

FOREIGN PATENT DOCUMENTS

| WO | WO 01/41672 | 6/2001 |
| WO | PCT/US2004/007318 | 1/2004 |

* cited by examiner

*Primary Examiner* — Ahmed Farah
(74) *Attorney, Agent, or Firm* — Kenneth Bassinger

(57) ABSTRACT

Methods of manipulating pulses of ultrasonic energy for use with an ophthalmic surgical device.

23 Claims, 23 Drawing Sheets

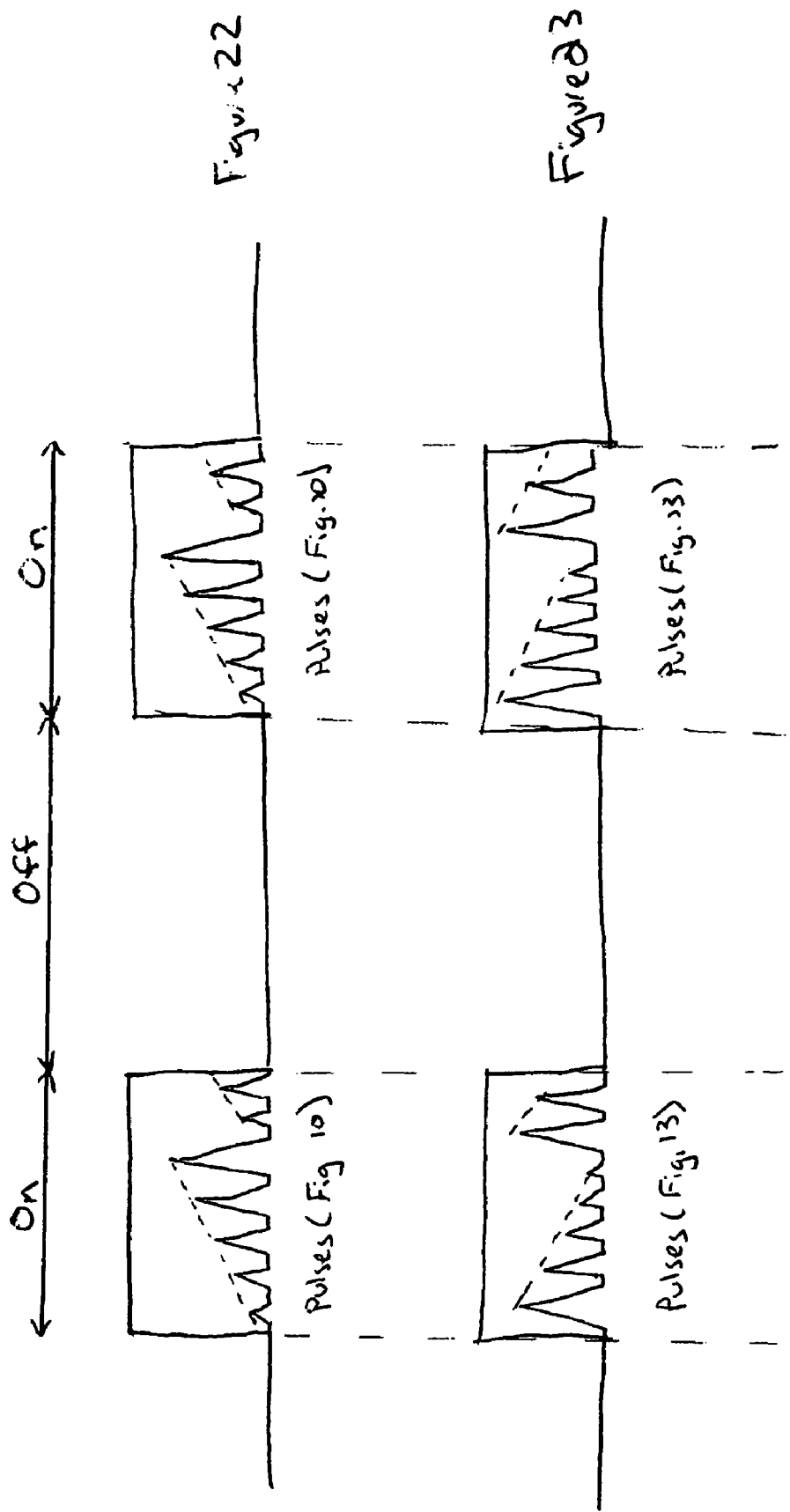

PULSE MANIPULATION FOR CONTROLLING A PHACOEMULSIFICATION SURGICAL SYSTEM

FIELD OF THE INVENTION

The present invention relates generally to the field of ophthalmic surgery and, more particularly, to a method of manipulating the shapes, sequences and durations of pulses of ultrasonic energy generated by an ultrasound handpiece of a phacoemulsification surgical system.

BACKGROUND

The human eye functions to provide vision by transmitting light through a clear outer portion called the cornea, and focusing the image by way of a lens onto a retina. The quality of the focused image depends on many factors including the size and shape of the eye, and the transparency of the cornea and lens. When age or disease causes the lens to become less transparent, vision deteriorates because of the diminished light that can be transmitted to the retina. This deficiency is medically known as a cataract. An accepted treatment for cataracts is to surgically remove the cataract and replace the lens with an artificial intraocular lens (IOL). In the United States, the majority of cataractous lenses are removed using a surgical technique called phacoemulsification. During this procedure, a thin cutting tip or needle is inserted into the diseased lens and vibrated ultrasonically. The vibrating cutting tip liquefies or emulsifies the lens, which is aspirated out of the eye. The diseased lens, once removed, is replaced by an IOL.

A typical ultrasonic surgical device suitable for an ophthalmic procedure includes an ultrasonically driven handpiece, an attached cutting tip, an irrigating sleeve or other suitable irrigation device, and an electronic control console. The handpiece assembly is attached to the control console by an electric cable or connector and flexible tubings. A surgeon controls the amount of ultrasonic energy that is delivered to the cutting tip of the handpiece and applied to tissue by pressing a foot pedal to request power up to the maximum amount of power set on the console. Tubings supply irrigation fluid to and draw aspiration fluid from the eye through the handpiece assembly.

The operative part of the handpiece is a centrally located, hollow resonating bar or horn that is attached to piezoelectric crystals. The crystals are controlled by the console and supply ultrasonic vibrations that drive both the horn and the attached cutting tip during phacoemulsification. The crystal/horn assembly is suspended within the hollow body or shell of the handpiece by flexible mountings. The handpiece body terminates in a reduced diameter portion or nosecone at the body's distal end. The nosecone is externally threaded to accept the irrigation sleeve. Likewise, the horn bore is internally threaded at its distal end to receive the external threads of the cutting tip. The irrigation sleeve also has an internally threaded bore that is screwed onto the external threads of the nosecone. The cutting tip is adjusted so that the tip projects only a predetermined amount past the open end of the irrigating sleeve.

In use, the ends of the cutting tip and the irrigating sleeve are inserted into a small incision in the cornea, sclera, or other location. One known cutting tip is ultrasonically vibrated along its longitudinal axis within the irrigating sleeve by the crystal-driven ultrasonic horn, thereby emulsifying the selected tissue in situ. The hollow bore of the cutting tip communicates with the bore in the horn that in turn communicates with the aspiration line from the handpiece to the console. Other suitable cutting tips include piezoelectric elements that produce both longitudinal and torsional oscillations. One example of such a cutting tip is described in U.S. Pat. No. 6,402,769 (Boukhny), the contents of which are incorporated herein by reference.

A reduced pressure or vacuum source in the console draws or aspirates emulsified tissue from the eye through the open end of the cutting tip, the cutting tip and horn bores and the aspiration line, and into a collection device. The aspiration of emulsified tissue is aided by a saline solution or other irrigant that is injected into the surgical site through the small annular gap between the inside surface of the irrigating sleeve and the cutting tip.

One known technique is to make the incision into the anterior chamber of the eye as small as possible in order to reduce the risk of induced astigmatism. These small incisions result in very tight wounds that squeeze the irrigating sleeve tightly against the vibrating tip. Friction between the irrigating sleeve and the vibrating tip generates heat. The risk of the tip overheating and burning tissue is reduced by the cooling effect of the aspirated fluid flowing inside the tip.

Some known surgical systems use "pulse mode" in which the amplitude of fixed-width pulses can be varied using a controller, such as a foot pedal. Other known surgical systems utilize "burst mode" in which each pulse of a series of periodic, fixed width, constant amplitude pulses is followed by an "off" time. The off time can be varied using a controller. Other known systems use pulses having an initial maximum power level followed by a lower power level. For example, Publication No. PCT/US2004/007318 describes pulses that rise from zero to an initial, maximum power level, and then subsequently decrease to lower levels.

While known surgical systems have been used effectively, they can be improved by allowing greater control over pulses for use with various surgical devices and applications. For example, known systems that use square or rectangular pulses typically have power levels that increase very quickly to a maximum power level. Sharp pulse transitions can reduce the ability to hold and emulsify lens material. More specifically, when lens material is held at a tip of an ultrasound hand piece by vacuum, the very fast (almost immediate) ramping of a pulse to a maximum power level can displace or push the lens material away from the tip too quickly. This, in turn, complicates cutting of the lens material. In other words, rapid power transitions can create an imbalance between vacuum at the ultrasonic tip that holds or positions the lens material and the ability to emulsify lens material.

Other known systems operate at high power levels when less power or no power would suffice. For example, with rectangular pulses, an initial high power level may be needed to provide power to emulsify lens material. However, after the material is pushed away or emulsified, additional power may not be needed. Rectangular pulses that apply the same amount of power after movement or emulsification of lens material can result in excessive heat being applied to tissue, which can harm the patient.

Further, pulse patterns that are used by some known surgical systems do not adequately reduce cavitation effects. Cavitation is the formation of small bubbles resulting from the back and forth movement of an ultrasonic tip. This movement causes pockets of low and high pressure. As the ultrasonic tip moves backwards, it vaporizes liquid due to a low local pressure and generates bubbles. The bubbles are compressed as the tip moves forwards and implode. Imploding bubbles can create unwanted heat and forces and complicate surgical procedures and present dangers to the patient.

Therefore, a need continues to exist for methods that allow pulse shapes and durations to be manipulated for different phacoemulsification applications and procedures.

SUMMARY

In accordance with one embodiment, a method of generating energy for use with an ophthalmic surgical device includes generating a group of pulses having at least one pulse that includes a programmed substantially linear component and at least one pulse having an attribute that is different from the pulse having the programmed substantially linear component. According to another embodiment, a method of generating energy for use with an ophthalmic surgical device includes generating a group of pulses, the group of pulses. The group of pulses includes at least one pulse that includes a programmed substantially linear component; and at least one pulse that does not include a programmed substantially linear component. Each pulse differs from at least one other pulse in the group in at least one manner. In accordance with yet a further embodiment, a method of generating energy for use with an ophthalmic surgical device includes generating a group of pulses including one or more rectangular pulses and one or more pulses having a programmed substantially linear component.

In various embodiments, the group of pulses, such as two to ten pulses, can have having sequentially different power, e.g., sequentially decreasing and sequentially increasing power. The pulses in the group can have the same or different amplitudes. The pulses in the group can have different on-times. The pulses can have the same or different shapes. A pulse in the group can be a rectangular pulse or a triangular pulse. The triangular pulse can have one or two programmed linear components, e.g., programmed linear rise and/or decay components. A pulse can also include a programmed non-linear decay component. A controller, such as a foot pedal, can be used to change the amplitude of the group of pulses.

BRIEF DESCRIPTION OF THE DRAWINGS

Referring now to the drawings, in which like reference numbers represent corresponding parts throughout and in which:

FIG. 22 illustrates packets of pulses of ultrasonic energy shown in FIG. 10; and FIG. 23 illustrates packets of pulses of ultrasonic energy shown in FIG. 13.

DETAILED DESCRIPTION OF ILLUSTRATED EMBODIMENTS

Figure 1:
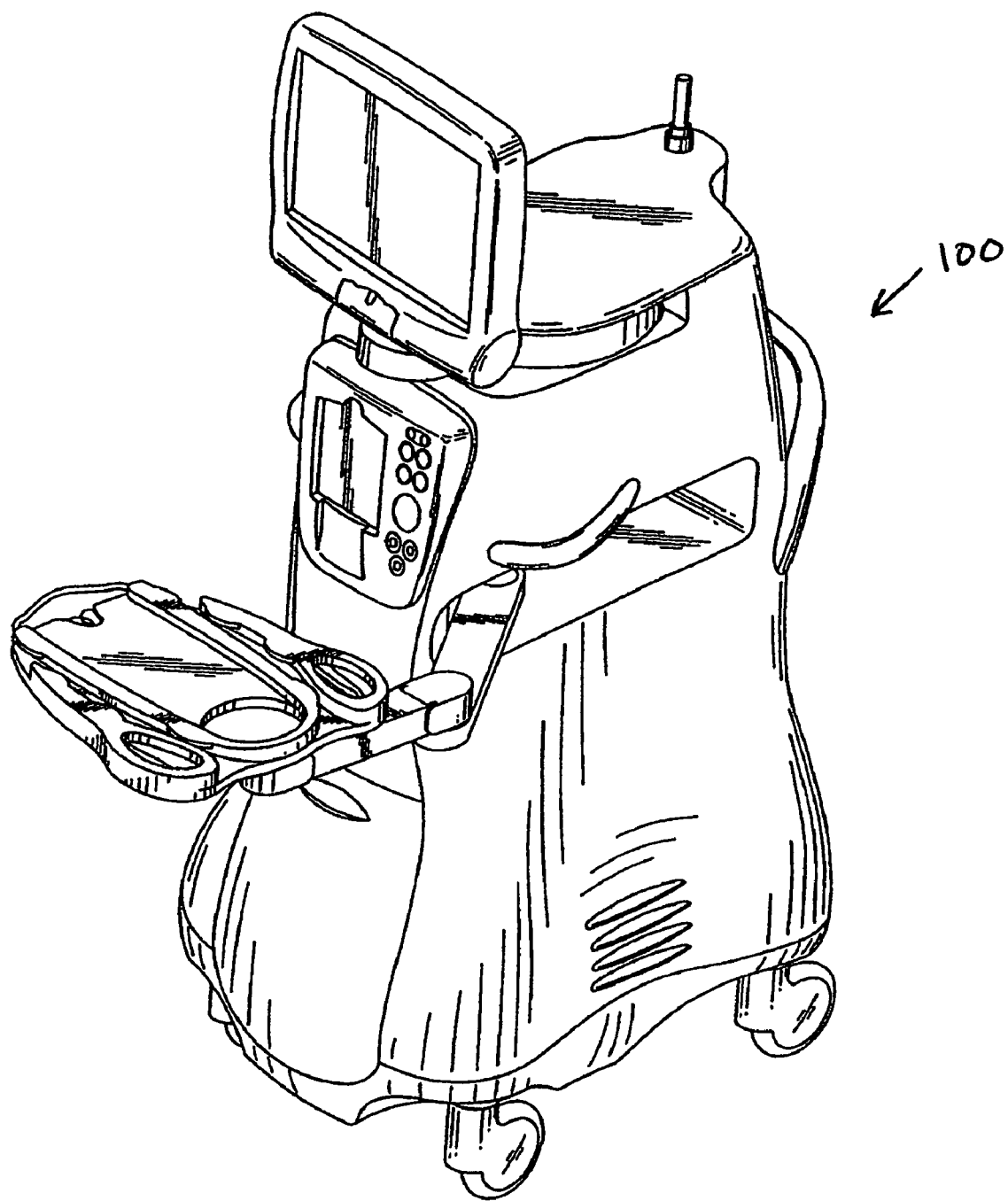
FIG. 1 illustrates an exemplary phacoemulsification surgical system that may be used with various embodiments.

This specification describes embodiments of methods of manipulating pulses of ultrasonic energy to control a surgical system for use in, for example, phacoemulsification surgery. Embodiments can be implemented on commercially available surgical systems or consoles through appropriate hardware and software controls. FIGS. 1 and 2 illustrate exemplary surgical systems.

Figure 2A:
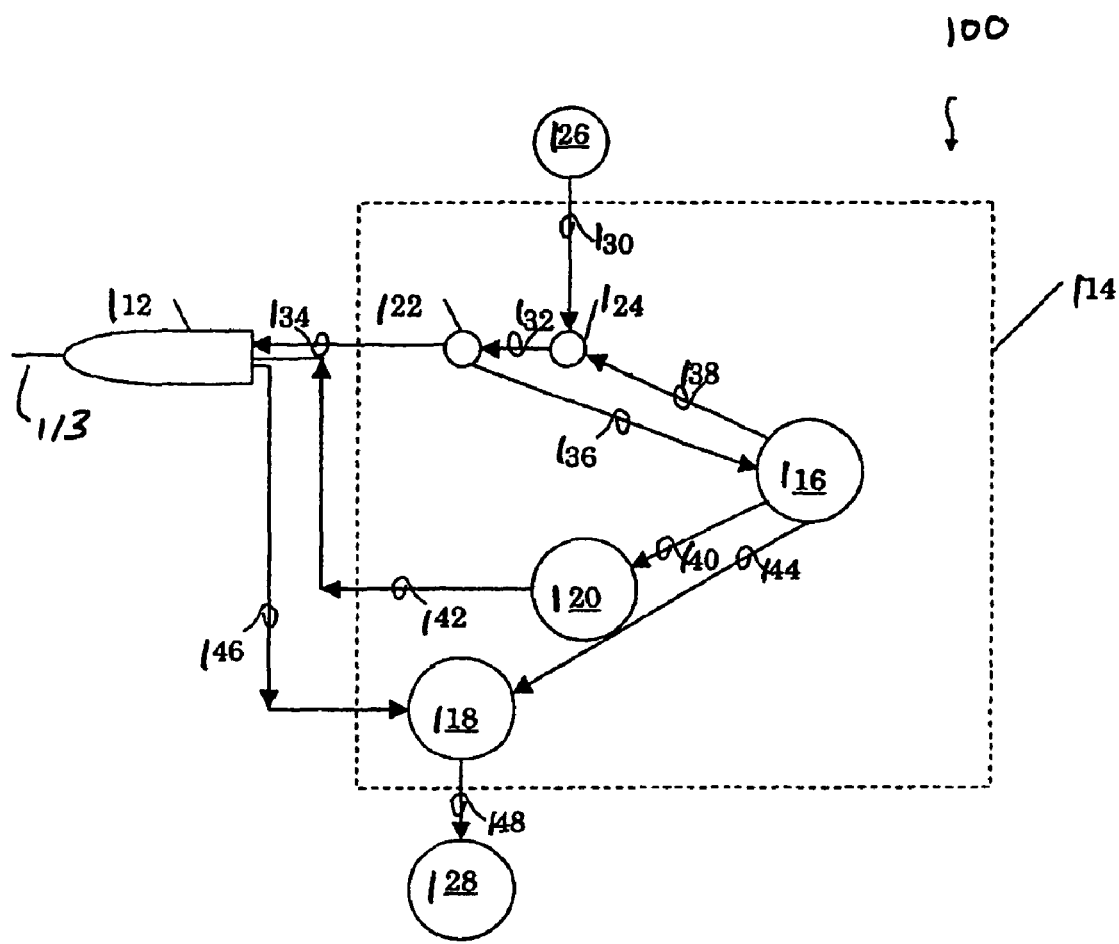
FIG. 2A is block diagram showing components of an exemplary phacoemulsification surgical system.

FIG. 1 illustrates one suitable system and represents the INFINITI® Vision System available from Alcon Laboratories, Inc., 6201 South Freeway, Q-148, Fort Worth, Tex. 76134. FIG. 2A illustrates an exemplary control system 100 that can be used with this system.

The control system 100 is used to operate an ultrasound handpiece 112 and includes a control console 114, which has a control module or CPU 116, an aspiration, vacuum or peristaltic pump 118, a handpiece power supply 120, an irrigation flow or pressure sensor 122 (such as in the Infiniti® system) and a valve 124. Various ultrasound handpieces 112 and cutting tips can be utilized including, but not limited to, handpieces and tips described in U.S. Pat. Nos. 3,589,363; 4,223,676; 4,246,902; 4,493,694; 4,515,583; 4,589,415; 4,609,368; 4,869,715; 4,922,902; 4,989,583; 5,154,694 and 5,359,996, the contents of which are incorporated herein by reference. The CPU 116 may be any suitable microprocessor, microcontroller, computer or digital logic controller. The pump 118 may be a peristaltic, a diaphragm, a Venturi or other suitable pump. The power supply 120 may be any suitable ultrasonic driver. The irrigation pressure sensor 122 may be various commercially available sensors. The valve 124 may be any suitable valve such as a solenoid-activated pinch valve. An infusion of an irrigation fluid, such as saline, may be provided by a saline source 126, which may be any commercially available irrigation solution provided in bottles or bags.

In use, the irrigation pressure sensor 122 is connected to the handpiece 112 and the infusion fluid source 126 through irrigation lines 130, 132 and 134. The irrigation pressure sensor 122 measures the flow or pressure of irrigation fluid from the source 126 to the handpiece 112 and supplies this information to the CPU 116 through the cable 136. The irrigation fluid flow data may be used by the CPU 116 to control the operating parameters of the console 114 using software commands. For example, the CPU 116 may, through a cable 140, vary the output of the power supply 120 being sent to the handpiece 112 and the tip 113 though a power cable 142. The CPU 116 may also use data supplied by the irrigation pressure sensor 122 to vary the operation of the pump 118 and/or valves through a cable 144. The pump 118 aspirates fluid from the handpiece 112 through a line 146 and into a collection container 128 through line 148. The CPU 116 may also use data supplied by the irrigation pressure sensor 122 and the applied output of power supply 120 to provide audible tones to the user. Additional details concerning such surgical systems can be found in U.S. Pat. No. 6,179,808 (Boukhny, et al.) and U.S. Pat. No. 6,261,283 (Morgan, et al.), the entire contents of which are incorporated herein by reference.

Figure 2B:
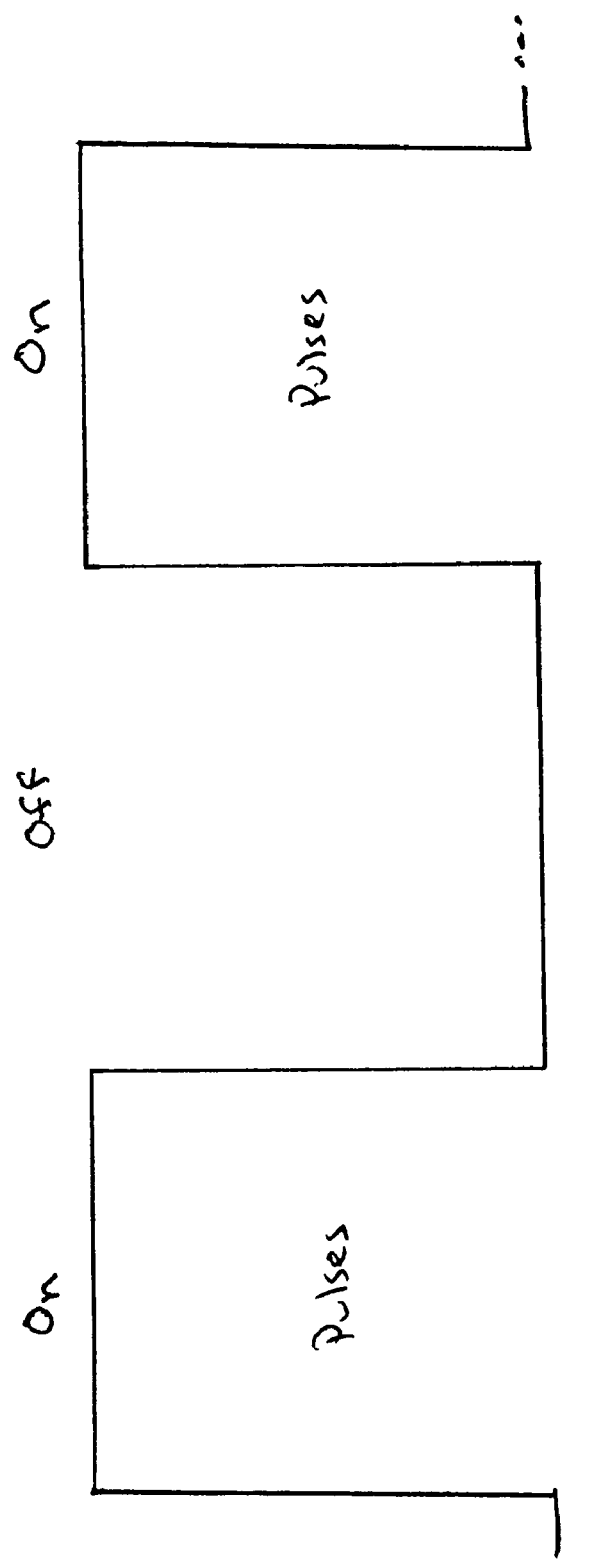
FIGS. 2B and 2C illustrate pulses for use with a phacoemulsification surgical system.
Figure 2C:
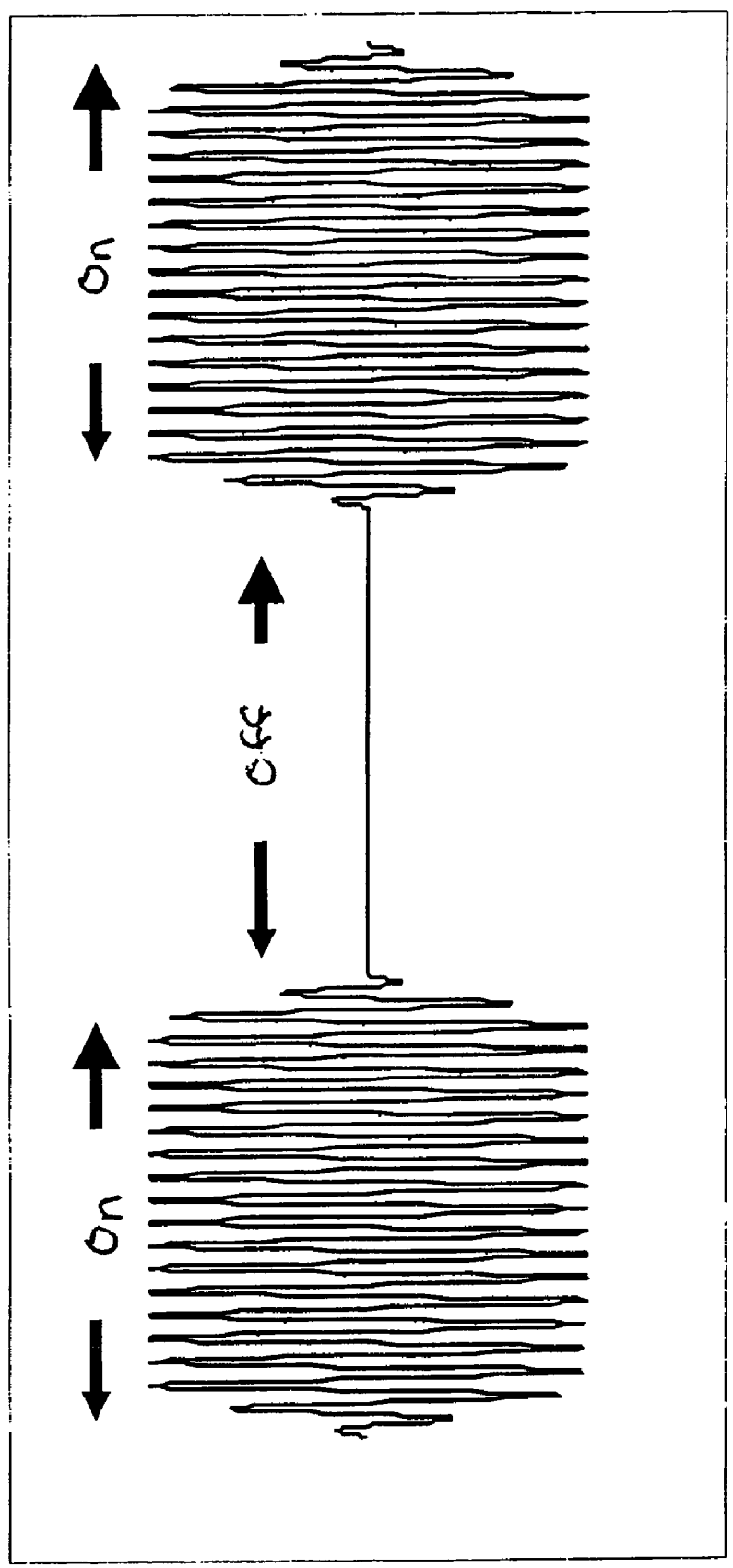

The control console 114 can be programmed to control and manipulate pulses that are delivered to the handpiece 112 and, in turn, control the power of the pulses of the handpiece that is used during surgery. Referring to FIGS. 2B and 2C, the pulses are generated in packets or in on periods and off periods. In the illustrated example, the pulses have a 50% duty cycle. Indeed, various on-times, off-times and duty cycles can be used for different applications.

The following description assumes that a maximum power level of 100% is the maximum attainable power (i.e., maximum stroke or displacement of the ultrasonic tip). In other words, 50% power refers to half of the maximum attainable power. Power levels are represented as a percentage (%) of the maximum attainable power. Embodiments of pulse manipulation that can be used with the exemplary phacoemulsification surgical system described above are illustrated in FIGS. 3-21, which can be organized as micro-bursts or packets of pulses, as shown in FIGS. 2B and 2C. The packets or bursts of pulses are provided to the ultrasound handpiece, which generates a generally corresponding output at the ultrasonic tip.

Figure 3:
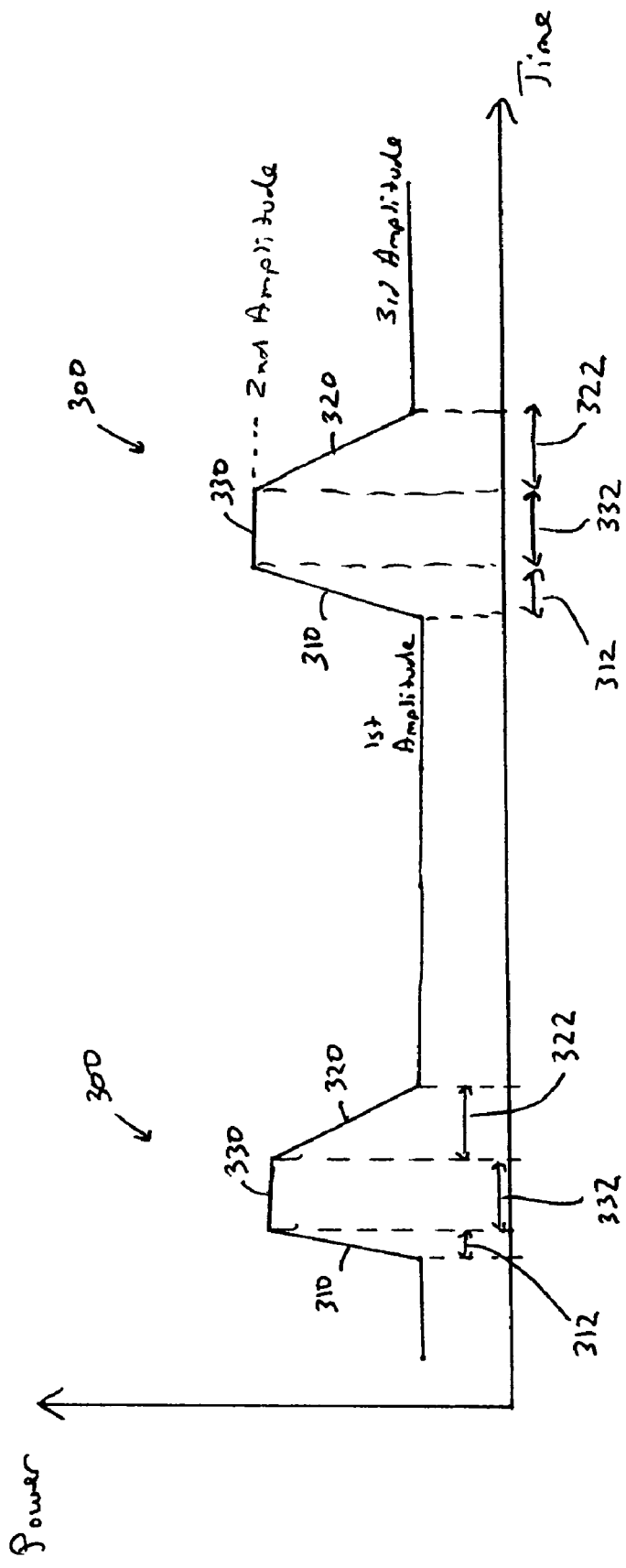
FIG. 3 illustrates pulses having linear rise and linear decay components and a constant maximum amplitude component according to one embodiment.

Referring to FIG. 3, according to one embodiment, one or both of the rise and decay components 310 and 312 of each pulse 300 can be programmed separately from a natural rise and natural decay. For example rise and decay components 310 and 312 can be programmed with linear and/or non-linear functions separately from natural rise and decay times that occur due to switching an amplifier on and off to generate pulses. Persons skilled in the art will appreciate that some pulses (e.g., square and rectangular pulses) are typically represented as "ideal" square or rectangular pulses having immediate and sharp transitions between low and maximum power levels. In practice, however, such pulses have natural rise and decay times, e.g., exponential rise and decay times, which are caused by a load or impedance. For example, typical natural decay times can be about 4 milliseconds (ms). Embodiments, in contrast, are directed to controlling linear rise and linear decay times separately from natural transitions that are caused by switching an amplifier on and off by setting or programming the rise and/or decay functions.

Controlling the rise and decay components 310 and 312 and rise and decay times 312 and 322 provides advantageously allows different pulse configurations to be generated for particular surgical applications and systems. For example, pulses having programmed rise components 310 that gradually increase in power allow the lens material to be positioned more accurately. Gradual power transitions, for example, do not prematurely push the lens material away from the tip of the handpiece. In contrast, known systems using pulses having sharp minimum to maximum transitions may inadvertently push lens material away from the tip too quickly, thus complicating the surgical procedure. Accordingly, pulses that include programmed rise components can improve the positioning and cutting of lens material and the effectiveness of surgical procedures. Further, programming decay components and pulse times allows less energy to be delivered to the eye, resulting in less heating of the tissue.

According to one embodiment, the programmed rise and/or decay component is programmed according to a linear function. In the embodiment illustrated in FIG. 3, each pulse 300 is programmed with two linear components—a linear rise component 310 and a linear decay component 320. The linear rise component 310 increases from a first amplitude to a second amplitude. An intermediate component 330 extends between the linear components 310 and 320 at a second amplitude. The decay component 330 decreases from the second amplitude to a third amplitude.

The linear rise component 310 has a linear rise time 312, the linear decay component 320 has a linear decay time 322, and the maximum amplitude component 330 has a maximum amplitude or active or "on" time 332. Linear rise and linear decay times 312 and 322 can vary depending on the maximum power level of a pulse since more time is typically required to reach higher power levels.

In one embodiment, the linear rise time 312 can be programmed to be about 5 ms to about 500 ms. If a pulse must reach 100% power, the duration of the linear rise time 312 may be longer. However, if the pulse must reach less than 100% power, then the linear rise time 312 can be shorter, e.g. less than or about 5 ms. Linear rise time 312 durations may increase with increasing power levels and can be appropriately programmed using the control console 114. If necessary, the rate at which the linear component increases can be limited to protect power components, such as an amplifier.

According to one embodiment, the linear decay time 322 can be programmed to be about 5 ms to about 500 ms. In one embodiment, the liner decay time 322 is programmed using the control console 114 so that power decays linearly and about 70% of the power dissipates in about 2 ms, and about 98% of the power dissipates in about 4 ms. The linear decay time 322 may be longer than, about the same as, or shorter than the linear rise time 312. For example, FIG. 3 illustrates the decay time 322 being longer than the rise time 312. The linear decay time 322 can be longer or slower than a natural decay time. The rise and decay rates may also be the same so that the pulse is symmetrical and has both programmed rise and decay components.

The maximum amplitude or active or "on" time 332 can vary with different applications. The maximum amplitude time can be about 5 ms to about 500 ms. In the illustrated embodiment, the intermediate component 330 has a constant amplitude (at the second amplitude). In an alternative embodiment, the duration of the maximum amplitude time can be less than 5 ms depending on, for example, required power and resulting heat considerations. In further alternative embodiments, the amplitude may vary across the intermediate component 330, e.g., increase or decrease between the first and second components 310 and 320.

In the illustrated embodiment, the rise component 310 begins at a non-zero level. In an alternative embodiment, the rise component 310 can begin at a zero level. The initial power level may depend on the particular surgical procedure and system configuration. Similarly, the decay component 320 can end at a zero or non-zero power level. FIG. 3 illustrates the first and third amplitudes being about the same. In alternative embodiments, they can be different. For example, the third amplitude at the end of the decay component 320 can be greater than the first amplitude.

In an alternative embodiment, the programmed rise and/or decay component can be a non-linear component. A non-linear component can be programmed according to logarithmic, exponential and other non-linear functions. For purposes of explanation, not limitation, FIG. 3 illustrates linear rise and decay components. However, one or both of the rise and decay components can be programmed with a non-linear function.

Figure 4:
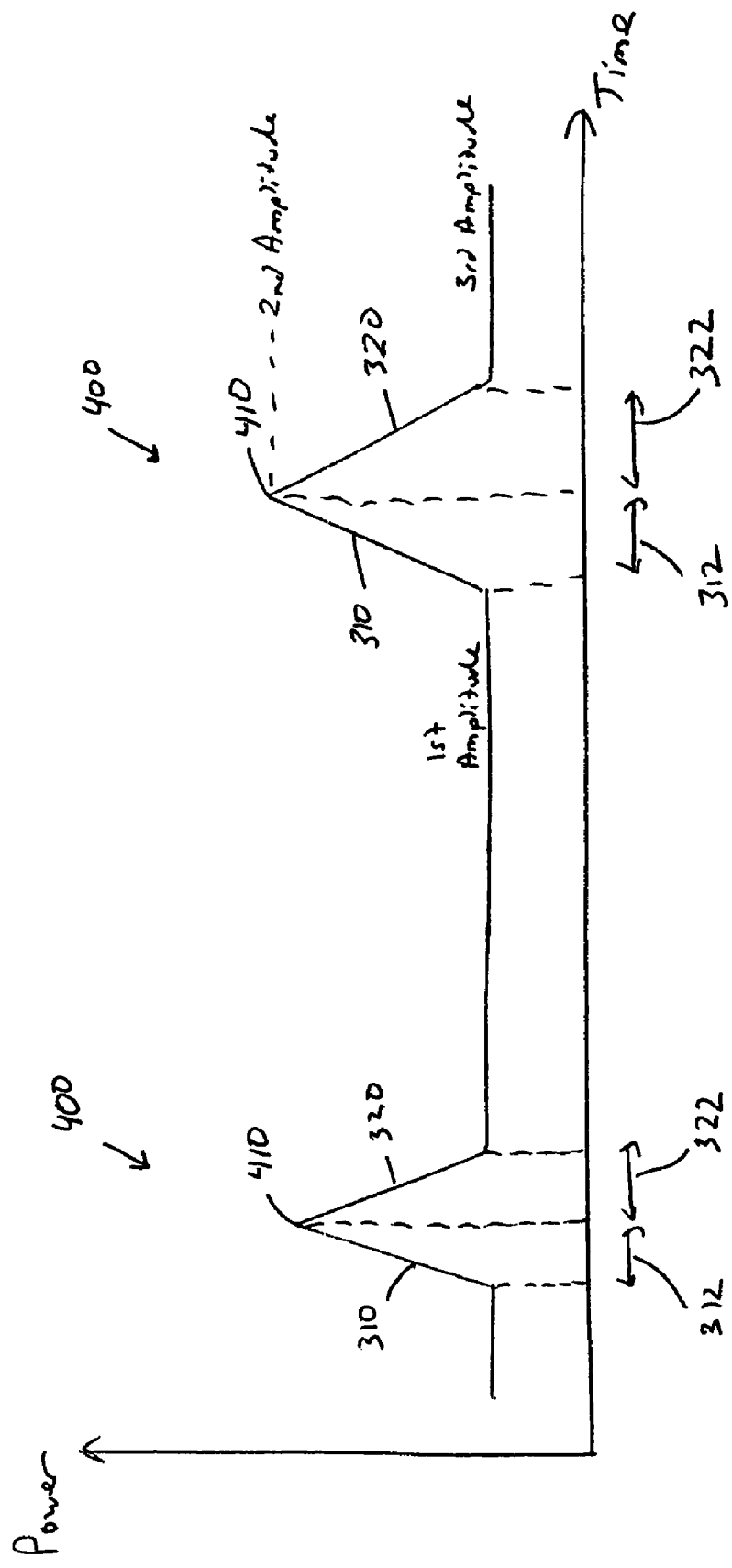
FIG. 4 illustrates pulses having linear rise and linear decay components that meet at a maximum point according to a further embodiment.

Referring to FIG. 4, according to an alternative embodiment, a pulse 400 is programmed with linear rise and linear decay components 310 and 320 that meet at a maximum point 410 at a second amplitude rather than having an intermediate component 330, as shown in FIG. 3. In the illustrated embodiment, the programmed rise and decay times 312 and 322 are equal. The linear rise and decay components 310 and 320 meet at a midpoint. In alternative embodiments, as discussed above with respect to FIG. 3, linear rise and decay times 312 and 322 can be programmed to be about 5 ms to about 500 ms. Thus, the rise and decay times may not be equal, and the maximum point 410 may not be a midpoint.

Referring to FIGS. 5-8, in alternative embodiments, pulses having one or more linear and/or non-linear components can be combined with other pulses and pulse patterns. For purposes of explanation, not limitation, FIGS. 5-8 illustrate pulses having programmed linear components, however, one or more programmed linear components can be replaced with a programmed non-linear component.

Figure 5:
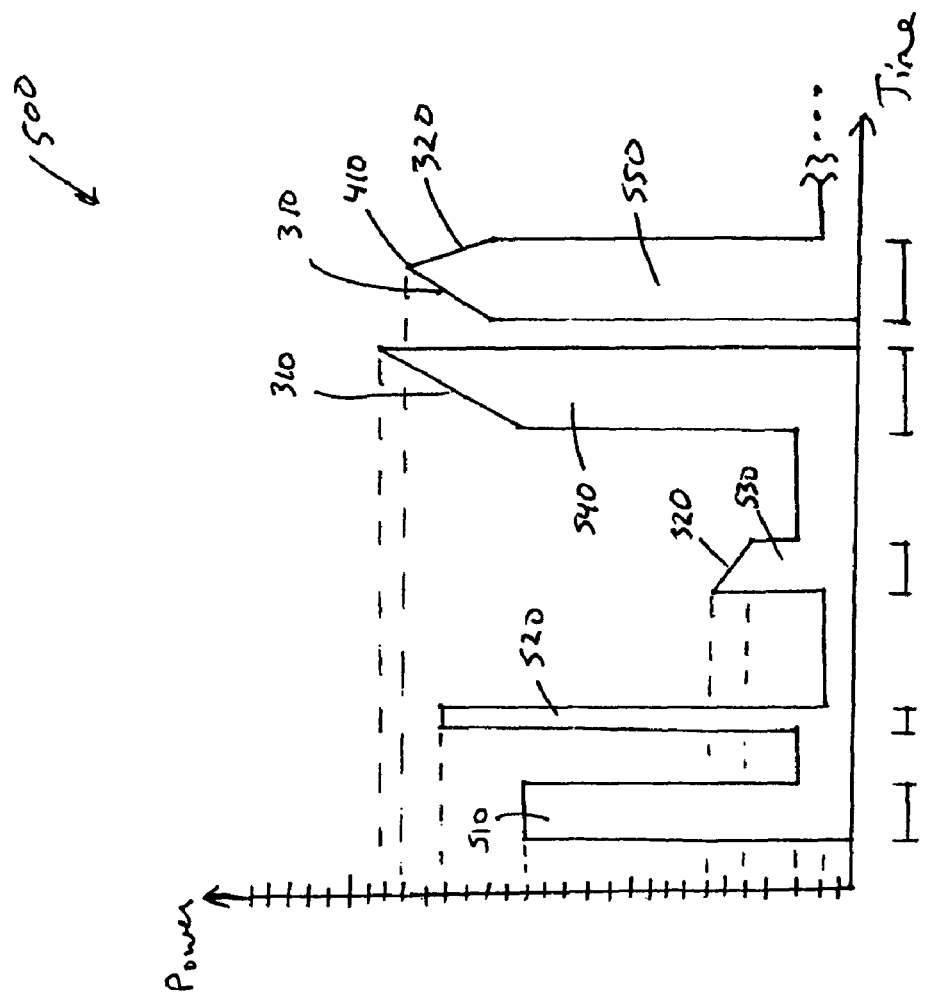
FIG. 5 illustrates a combination of pulses having a rectangular pulse and a pulse having a linear component according to another embodiment.

FIG. 5 illustrates a sequence or combination 500 of pulses having a first rectangular pulse 510, a second rectangular pulse 520, a pulse 530 having a linear decay component, a pulse 540 having a linear rise component and a pulse 550 having linear rise and linear decay components, similar to the pulse shown in FIG. 4.

Figure 6:
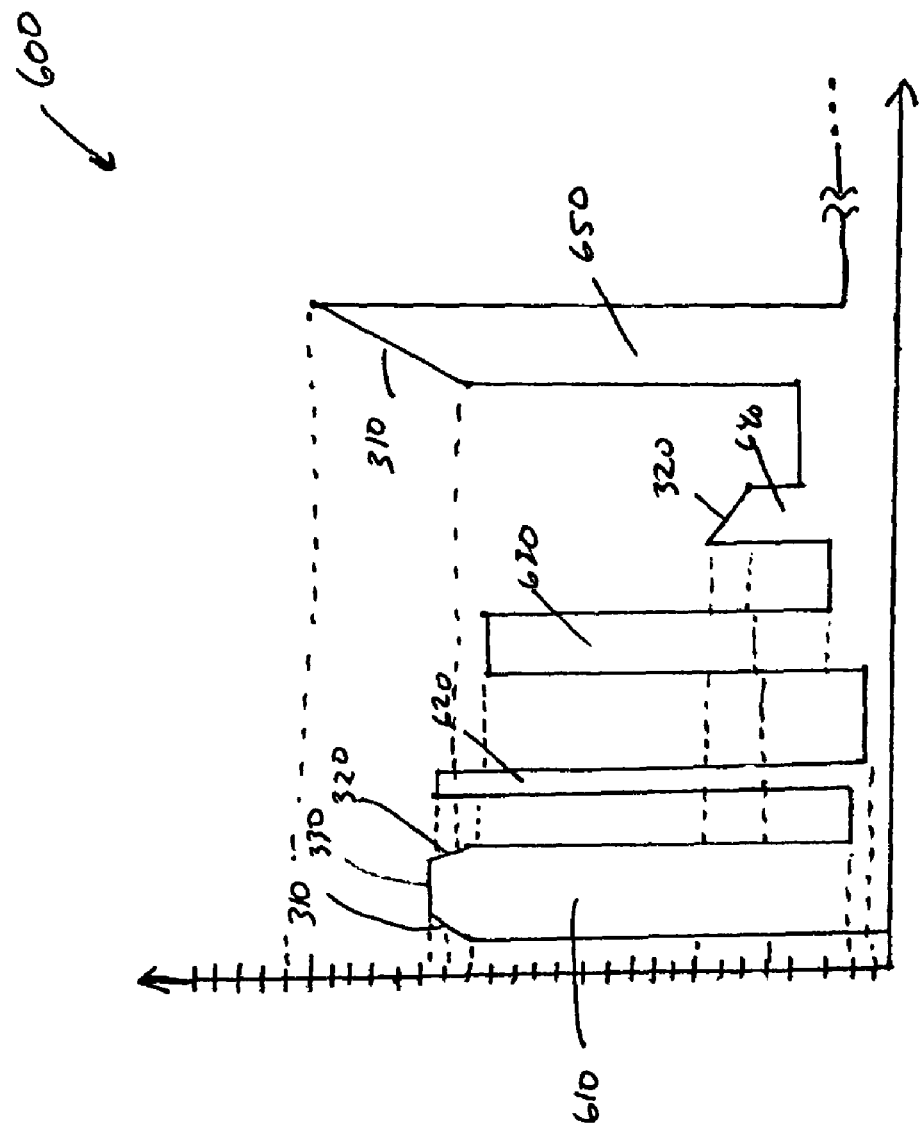
FIG. 6 illustrates a combination of pulses having a rectangular pulse and a pulse having a linear component according to further embodiment.

FIG. 6 illustrates a sequence or combination 600 of pulses according to another embodiment that includes a pulse 610 having linear rise and decay components and an intermediate component, similar to the pulse shown in FIG. 3, a rectangular pulse 620, a rectangular pulse 630 having a longer duration than pulse 620, a pulse 640 having a linear decay component and a pulse 650 having a linear rise component.

Figure 7:
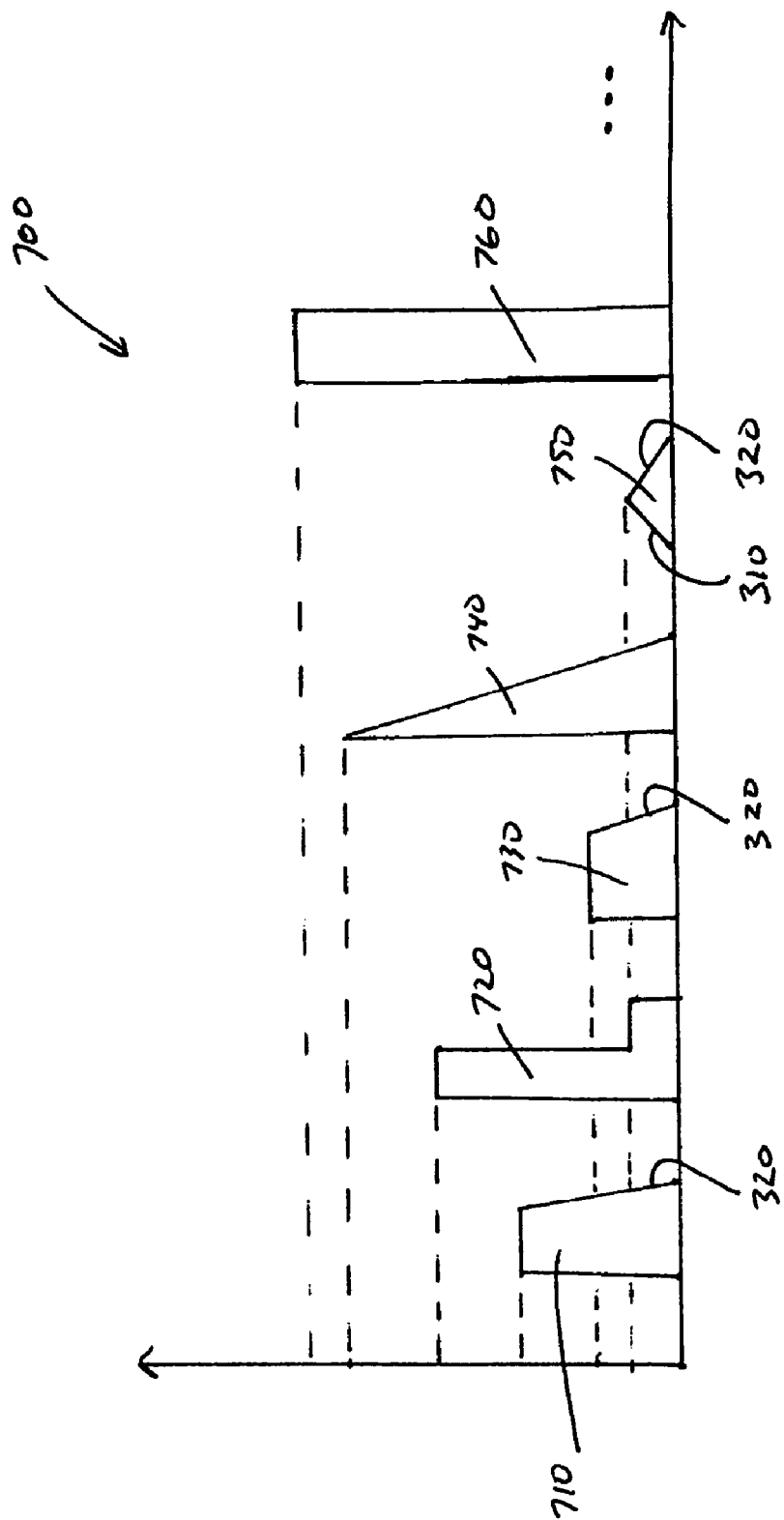
FIG. 7 illustrates a combination of pulses having a rectangular pulse and a pulse having a linear component according to yet a further embodiment.

FIG. 7 illustrates yet a further embodiment of a sequence or combination 700 of pulses that includes a pulse 710 having a linear decay component, a multi-segment rectangular pulse 720 having decreasing amplitude, a pulse 730 having a linear decay component, a pulse 740 having a linear decay component and a 750 pulse having both linear rise and linear decay components, similar to the pulse shown in FIG. 4, and another rectangular pulse 760.

Figure 8:
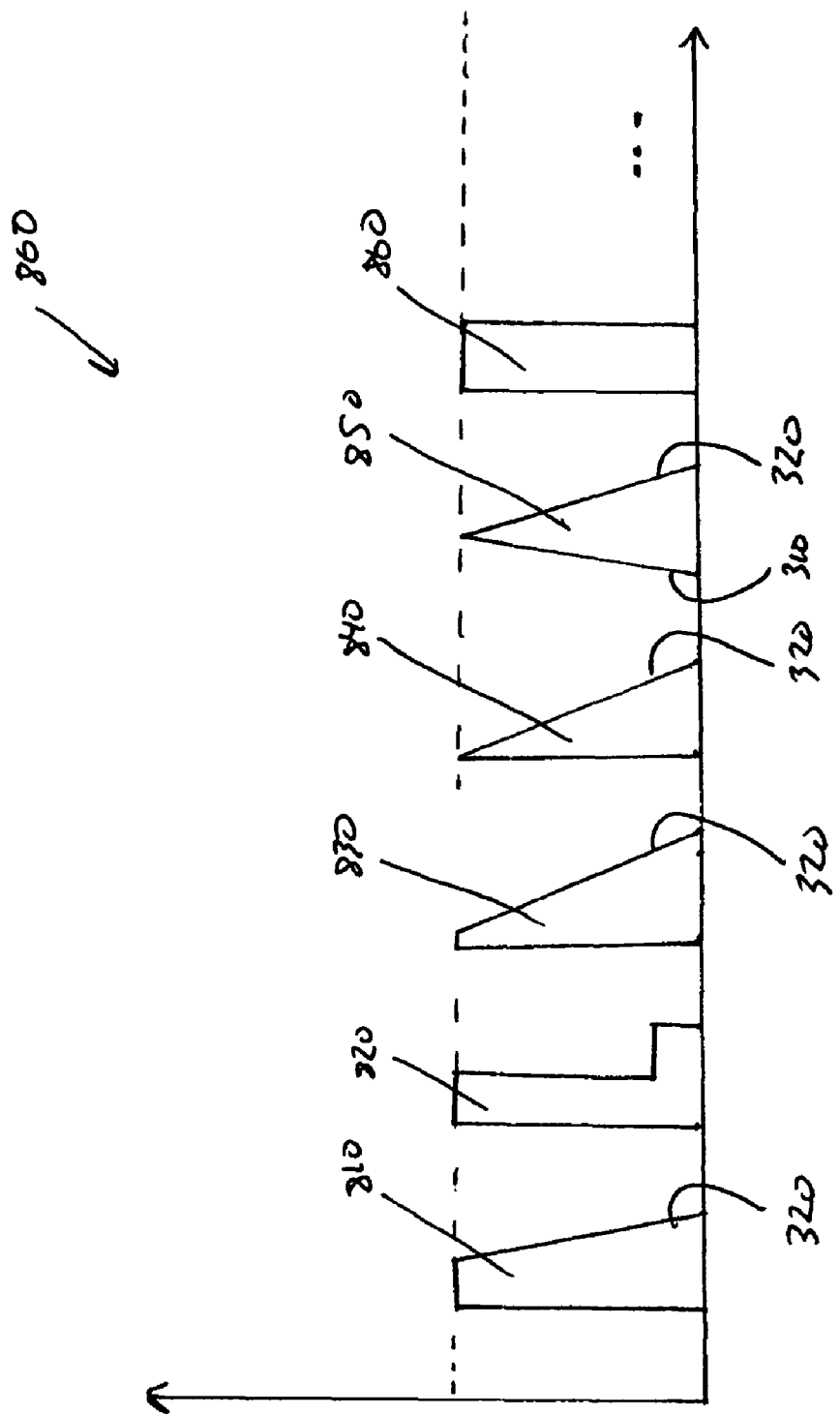
FIG. 8 illustrates a combination of pulses having a rectangular pulse and a pulse having a linear component at the same amplitude according to one embodiment.

FIG. 8 illustrates a further alternative embodiment of a sequence or combination 800 of pulses having the same maximum amplitude and at least one pulse having a linear component. In particular, FIG. 8 illustrates a pulse 810 having a linear decay component, a multi-segment rectangular pulse 820 having decreasing amplitude, a pulse 810 having a linear decay component, a pulse 840 having a linear decay component, a pulse 850 having both linear rise and decay components, similar to the pulse shown in FIG. 4, and a rectangular pulse 860.

As illustrated in FIGS. 5-8, each pulse in a packet of pulses can have an attribute that differentiates it from other pulses, e.g., based on different amplitude, duration, shape, number of programmed linear components and/or power. For example, pulse combinations can have pulses having different powers, amplitudes, shapes and durations. Further, pulse combinations can have different numbers of pulses, different numbers of rectangular and square pulses, different numbers of pulses having linear components, different numbers of pulses having one linear component, numbers of pulses having two linear components, and different numbers of pulses having two linear components and a constant amplitude component. Thus, embodiments surgeons to customize pulses to suite particular surgical procedures and phacoemulsification systems.

As shown in FIG. 5-8, the rectangular pulses and pulses having one or more linear component, can be placed in different positions and sequences, e.g., and at the beginning or end of a pulse sequence, or somewhere in between. The order of rectangular (or other shaped pulses) and pulses having a linear component can be altered depending on the surgical application and the system used. Certain pulses may be grouped together or commingled with other types of pulses.

For example, referring to FIG. 5, rectangular pulses 510 and 520 are grouped together and pulses 520, 530 and 540 having a linear component are grouped together. In an alternative embodiment, one or more non-rectangular pulses can be between the rectangular pulses so that the rectangular pulses are commingled with different types pulses. Similarly, one or more pulses that do not include a linear component can be placed between the pulses having a programmed linear component.

Figure 9:
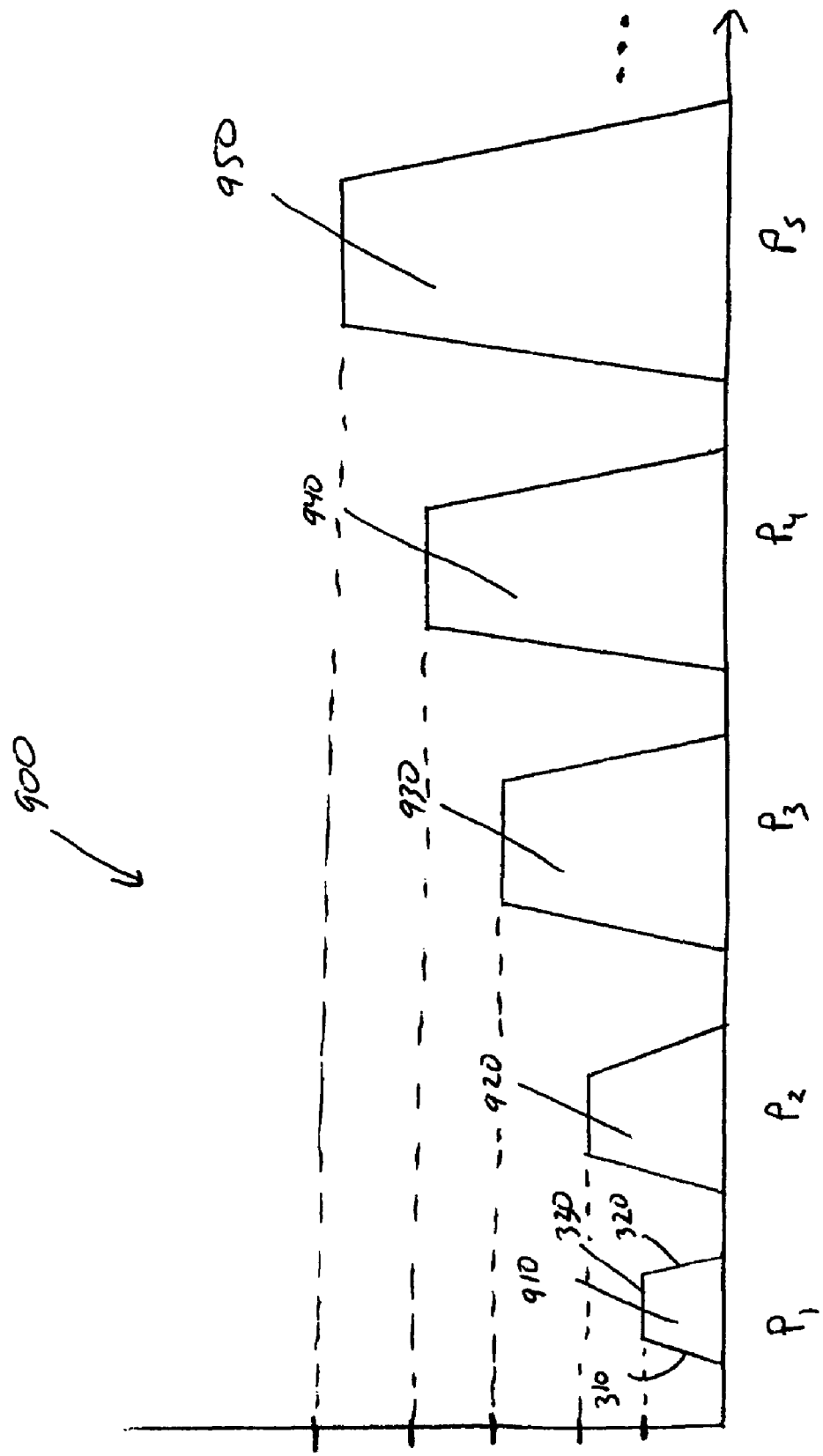
FIG. 9 illustrates pulses having linear rise and decay components, a constant amplitude component that has sequentially increasing power according to one embodiment.
Figure 10:
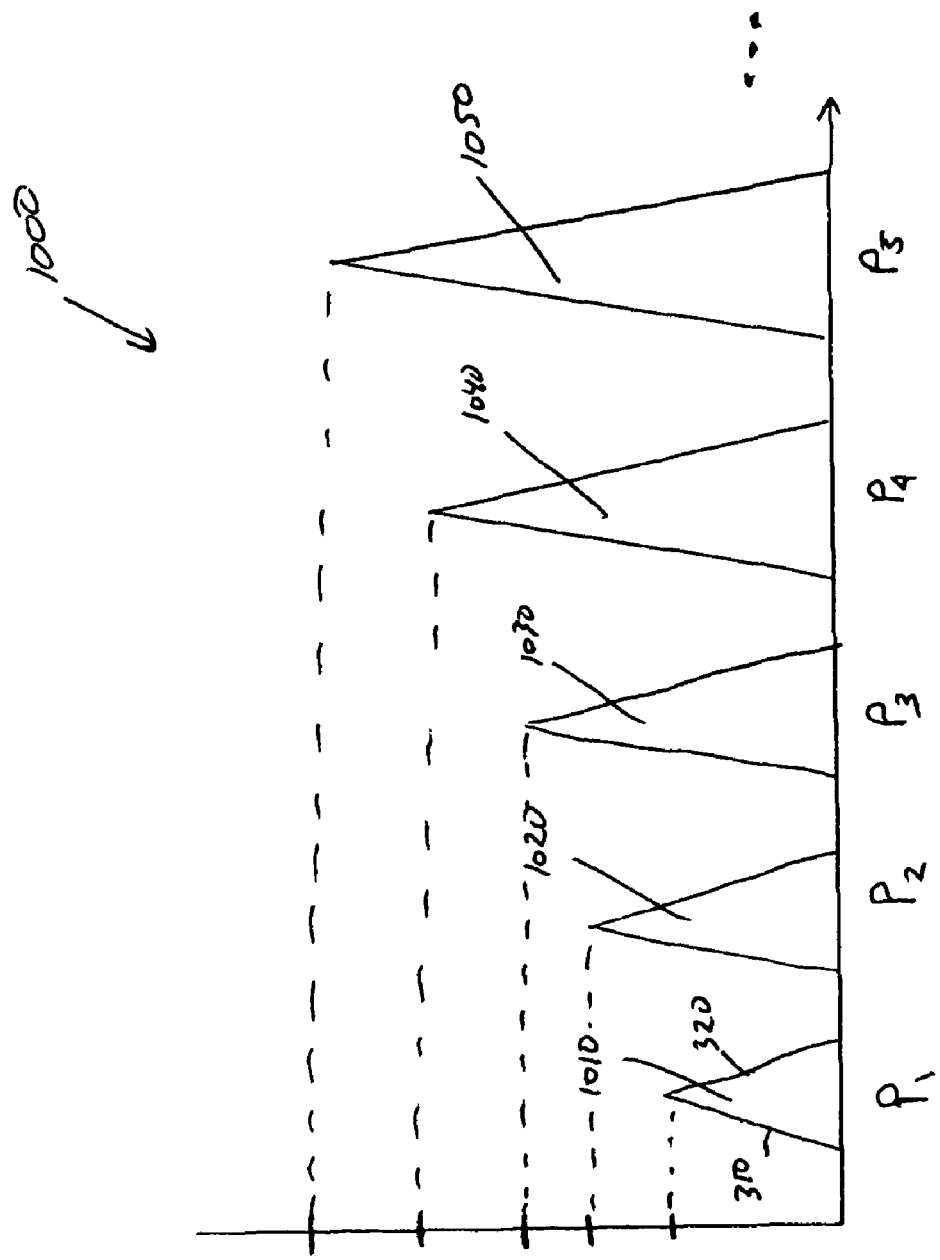
FIG. 10 illustrates pulses having linear rise and decay components that meet at a maximum point and that have sequentially increasing power according to a further embodiment.
Figure 11:
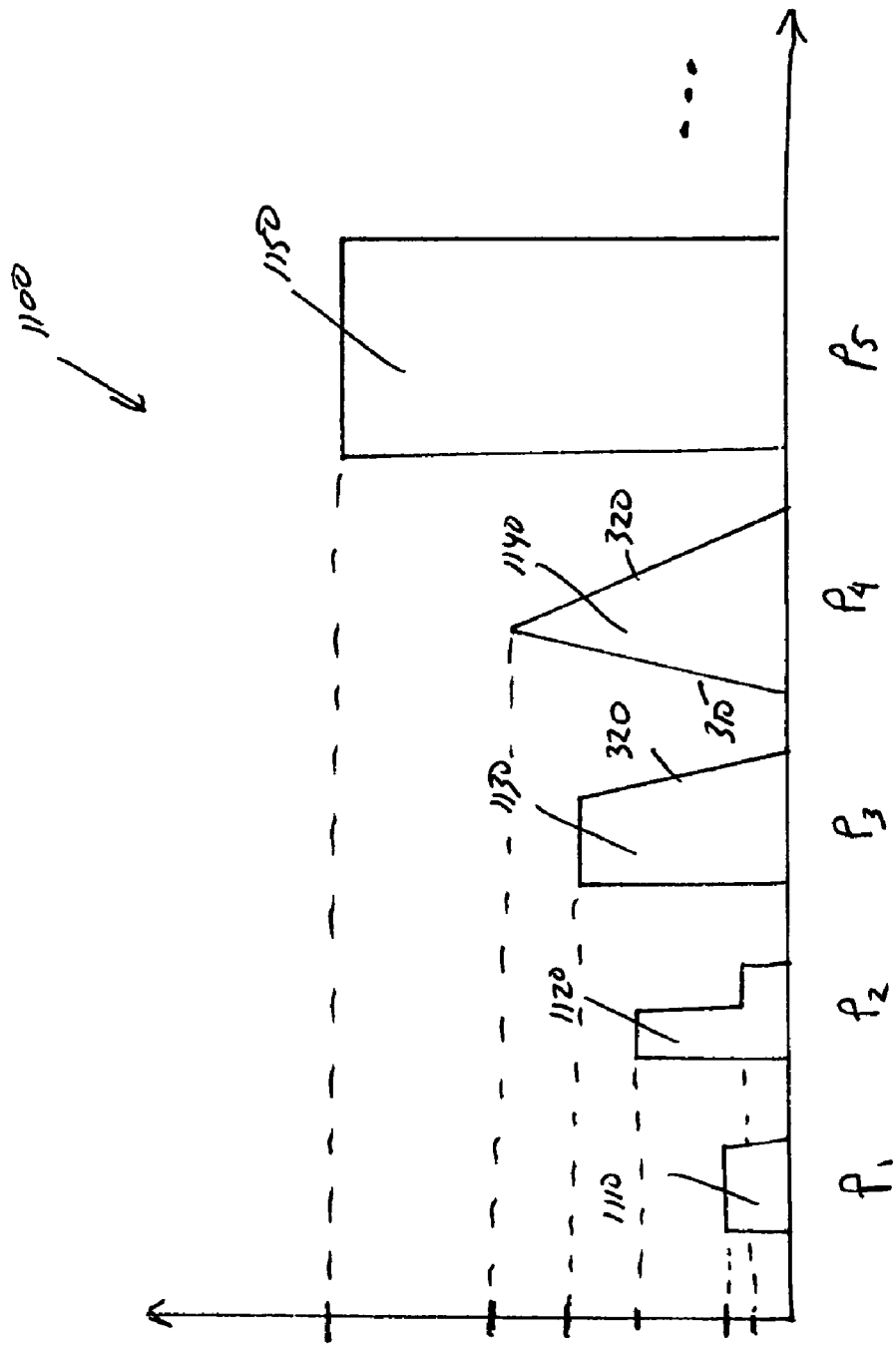
FIG. 11 illustrates a combination of rectangular pulses and pulses having a linear component having sequentially increasing power according to one embodiment.
Figure 12:
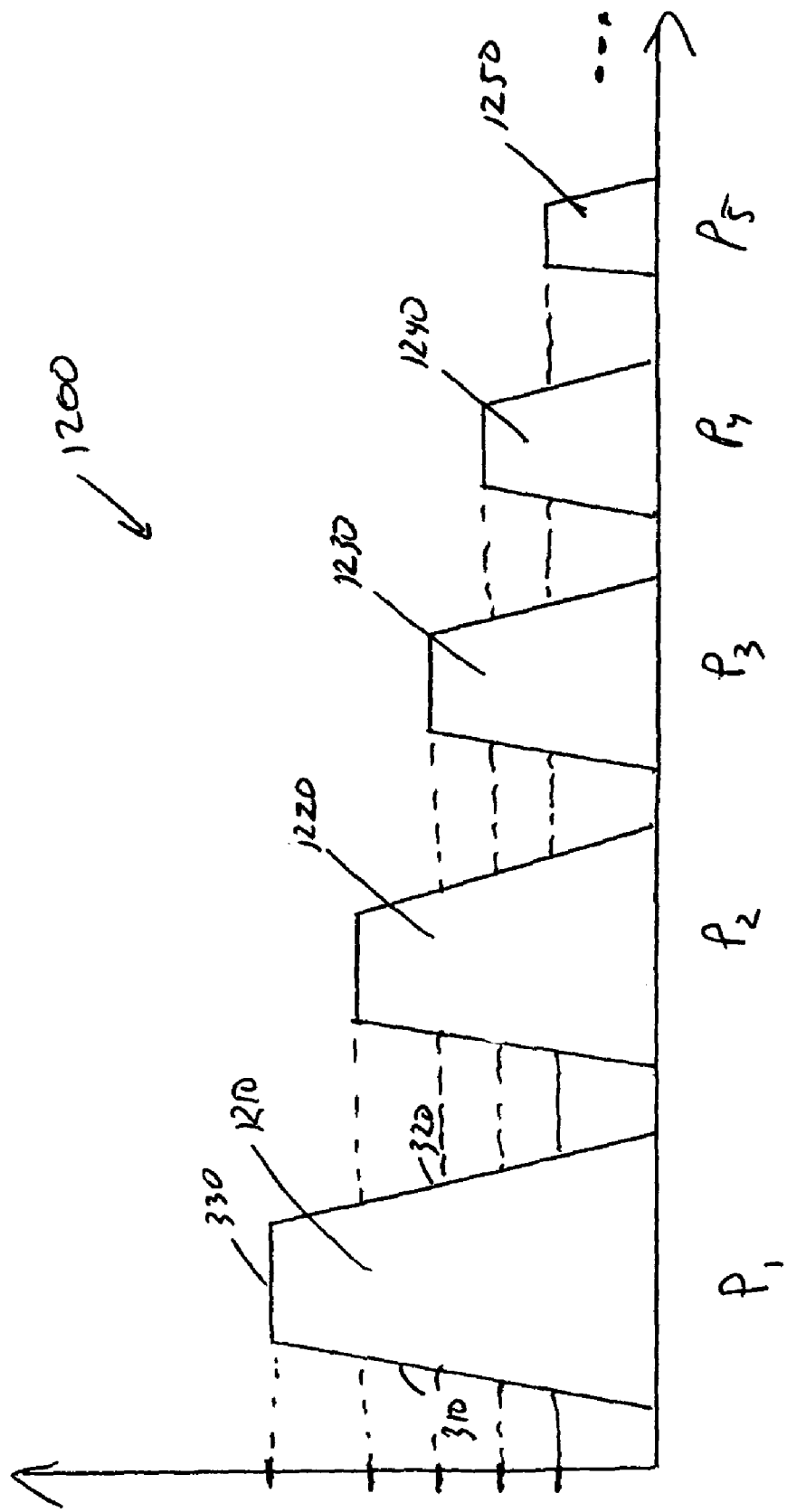
FIG. 12 illustrates pulses having linear rise and decay components, a constant amplitude component and sequentially decreasing power according to one embodiment.
Figure 13:
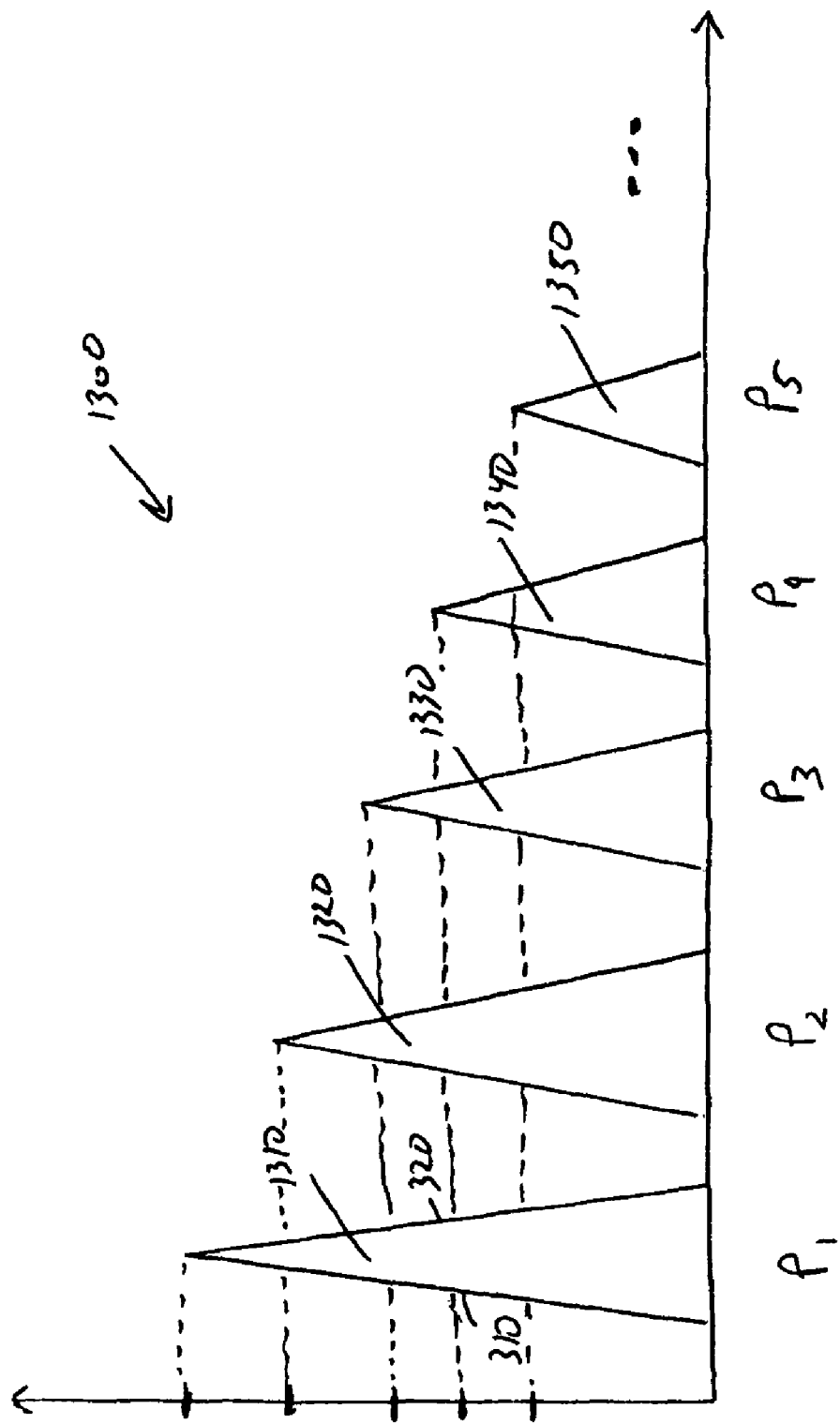
FIG. 13 illustrates pulses having linear rise and linear decay components that meet at a maximum point and having sequentially decreasing power according to a further embodiment.
Figure 14:
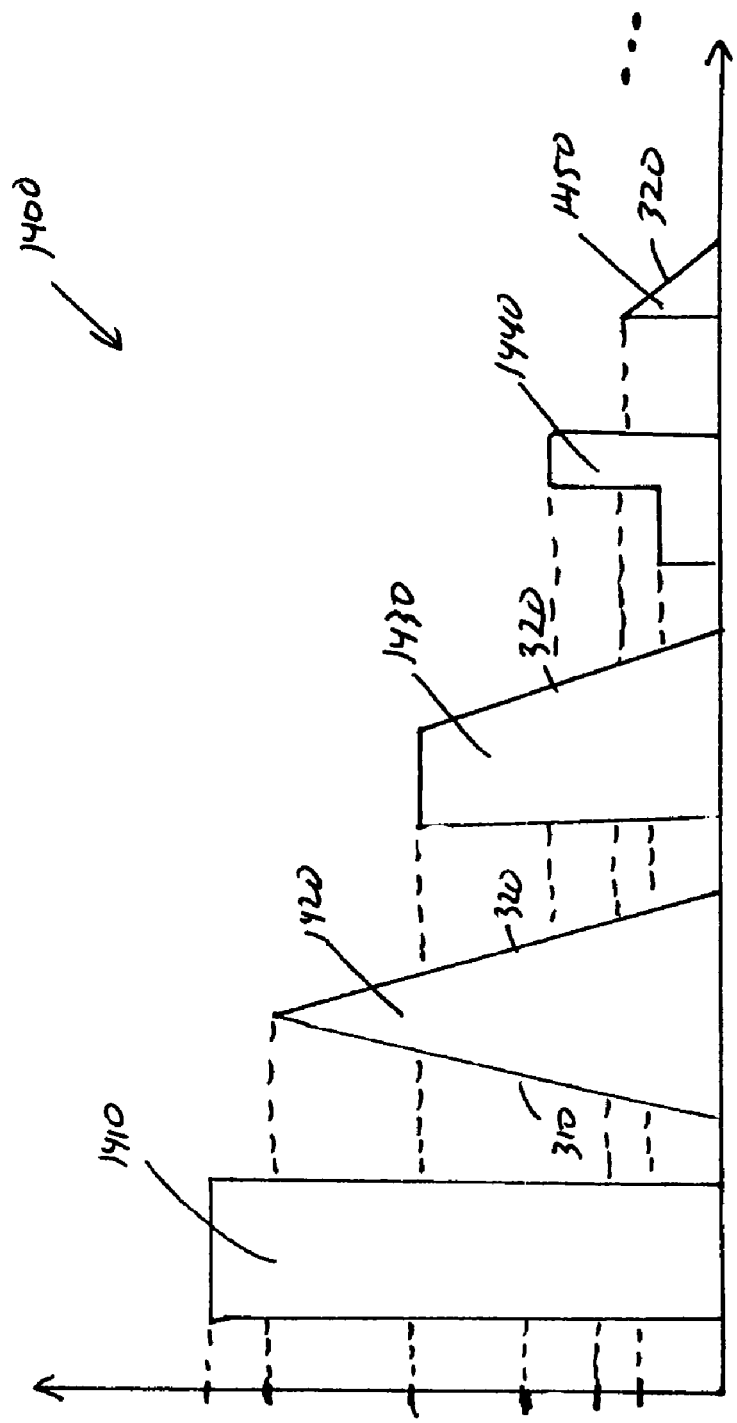
FIG. 14 illustrates a combination of rectangular pulses and pulses having a linear component and that have sequentially decreasing power according to another embodiment.

Referring to FIGS. 9-14, in alternative embodiments, pulses having a programmed linear component are included in a pattern of pulses in which each pulse has sequentially decreasing power or increasing power. FIGS. 9-11 illustrate pulse sequences in which each pulse has sequentially higher power, and FIGS. 12-14 illustrate pulse sequences in which each pulse has sequentially decreasing power.

Referring to FIG. 9, an alternative embodiment includes a sequence or combination 900 of pulses that includes pulses 910, 920, 930, 940 and 950, each of which is similar to the pulses shown in FIG. 3. Each successive pulse has a higher power (P1-P5) than a prior pulse. For example, pulse 930 has a power P3, which is greater than the power P2 of pulse 920.

FIG. 10 illustrates an alternative embodiment in which a sequence or combination 1000 of pulses includes pulses 1010, 1020, 1030, 1040, and 1050, each of which is similar to the pulses shown in FIG. 4. Each successive pulse has a higher power than a prior pulse.

FIG. 11 illustrates yet a further embodiment in which a sequence or combination 1100 of pulses includes pulses of various shapes and sizes, including rectangular pulses and at least one pulse having a linear component. Each successive pulse has a higher power than a prior pulse. A sequence or group of pulses having an initial low power level and subsequent increasing power levels may be useful to effectively hold and control lens material at a tip of an ultrasound handpiece, while gradually increasing power to emulsify lens material.

Referring to FIG. 12, according to another embodiment, a sequence or combination 1200 of pulses includes pulses

1210, 1220, 1230, 1240 and 1250, each of which is similar to the pulse shown in FIG. 3. Each pulse includes a programmed linear rise component 310 and a programmed linear decay component 320. Each pulse has reduced power relative to a prior pulse. For example, pulse P3 has less power than pulse P2, and pulse P4 has less power than pulse P3.

In an alternative embodiment, referring to FIG. 13, a sequence or group of pulses includes pulses 1310, 1320, 1330, 1340 and 1350. Each pulse is similar to the pulse shown in FIG. 4, and each pulse has reduced power relative to a prior pulse. FIG. 14 illustrates yet a further embodiment in which a sequence or combination 1400 of pulses 1410, 1420, 1430, 1440 and 1450 having reduced power over time. The combination 1400 includes pulses having different shapes and sizes, including rectangular pulses and pulses having a linear component.

Referring to FIGS. 15-19, alternative embodiments are directed to transforming pulses between different pulse modes in response to a controller, such as a foot pedal or foot switch. According to one embodiment, pulses are transferred between burst and pulse modes. Pulse patterns are shown relative to four foot pedal positions, which may or may not be defined by a detent or position indicator. Persons skilled in the art will appreciate that a foot pedal or switch can have other numbers of positions, and that the transitions described herein can be performed by pressing and releasing the foot pedal.

Figure 15:
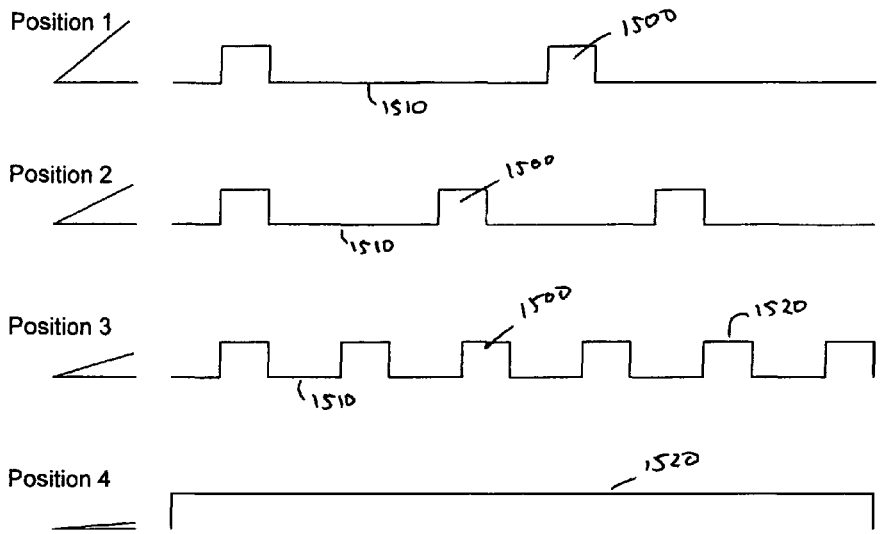
FIG. 15 illustrates known fixed burst mode pulses.
Figure 16:
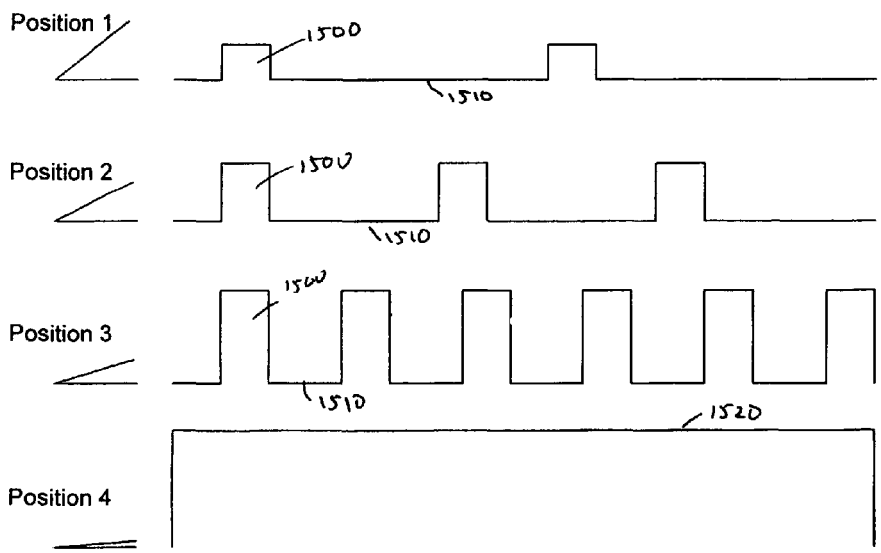
FIG. 16 illustrates known linear burst mode pulses.

Referring to FIG. 15, "burst" mode provides a series of periodic, fixed width, constant amplitude pulses 1500 of ultrasonic power, each of which is followed by an "off" time 1510. The off time 1510 between pulses 1500 is controlled by the surgeon's input by moving or pressing the foot pedal. In other words, in burst mode, each pulse 1500 has a fixed "on" time 1520, and a variable "off" time 1510, and the "off" time 1510 is adjusted based on the user's manipulation of the foot pedal. Burst mode pulses can have active times of about 5 ms to about 500 ms. The spacing between bursts or the "off-time" can be about 0 ms (when the foot pedal is fully depressed and power is continuous) to about 2.5 seconds. The off-time can depend on the application and system, for example, the desired amount of cooling or heat dissipation that may be required. Burst mode pulses may be "fixed burst" mode pulses as shown in FIG. 15 or, alternatively, be "linear burst" mode pulses as shown in FIG. 16. In fixed burst mode, pressing the foot pedal decreases the off-time 1510, while the amplitude of the pulses remains constant. In linear burst mode, pressing the foot pedal decreases the off-time 1500 and, in addition, adjusts the amplitude. In the illustrated embodiment, pressing the foot pedal increases the amplitude. Thus, in both fixed and linear burst modes, the power "Off" time 1510 can be adjusted, and the amplitude of pulses may or may not be adjusted.

More particularly, FIGS. 15 and 16 illustrate a foot pedal in four positions. The off time 1510 decreases when the foot pedal is initially at Position 1 and pressed further to Position 2. The number of fixed width, constant amplitude pulses 1500 increases as the foot pedal is pressed. As the foot pedal is pressed from Position 2 to Position 3, the off time 1510 eventually reaches a predetermined off time 1520, e.g., the on time 1520 or another suitable time. Pressing the foot pedal further from position 3 to position 4 reduces the off time 1510 to zero, i.e., a 100% on-time 1520 (continuous mode). A similar process is illustrated in FIG. 16, except that the pulses are linear burst mode pulses, and the amplitude of the pulses also increases as the foot pedal is moved among different positions.

Figure 17:
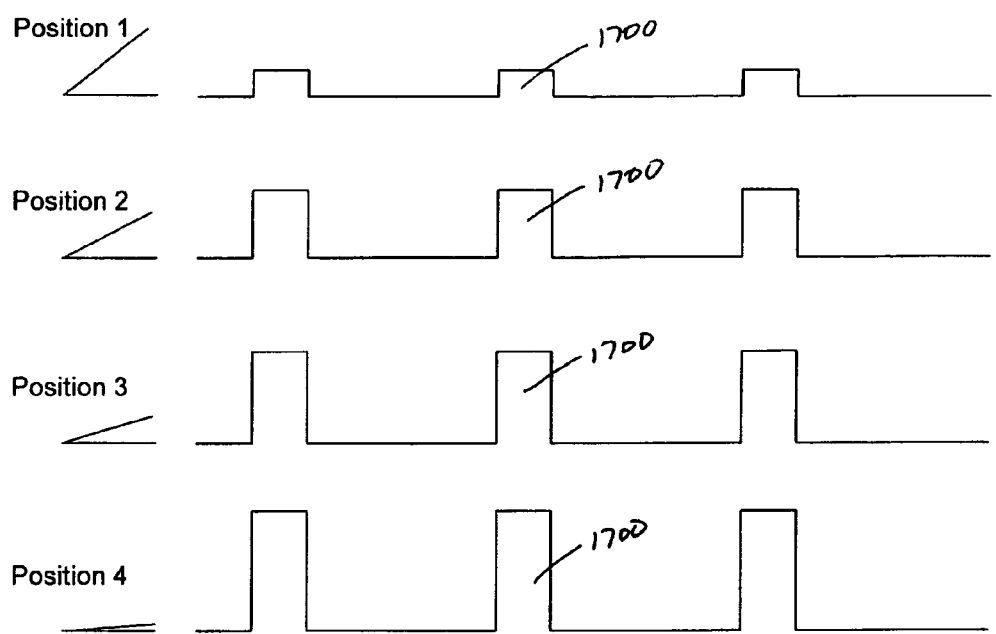
FIG. 17 illustrates known pulse mode pulses.

Referring to FIG. 17, in "pulse" mode, the amplitude of fixed-width pulses 1700 changes according to the position of the foot pedal. In the illustrated embodiment, the amplitude increases by pressing the foot pedal.

Figure 18:
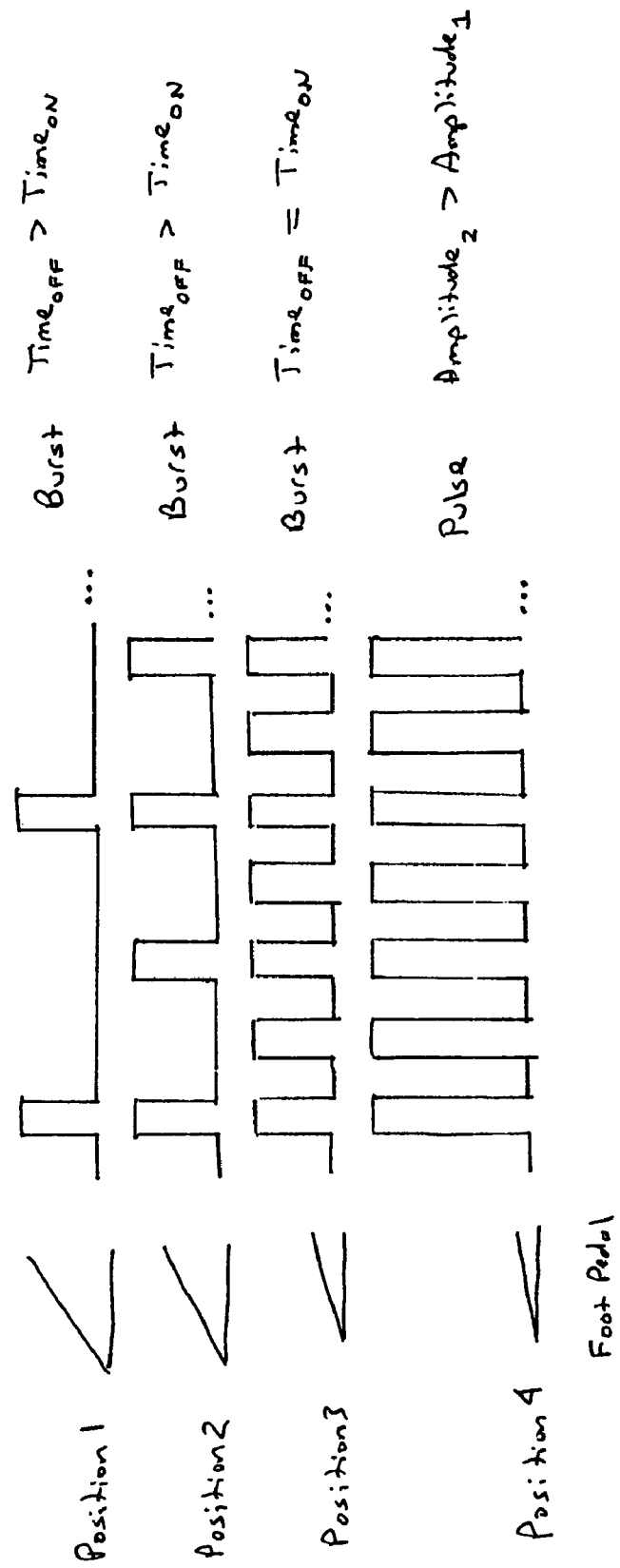
FIG. 18 illustrates continuous transformation of burst mode pulses to pulse mode pulses in response to a controller according to one embodiment.
Figure 19:
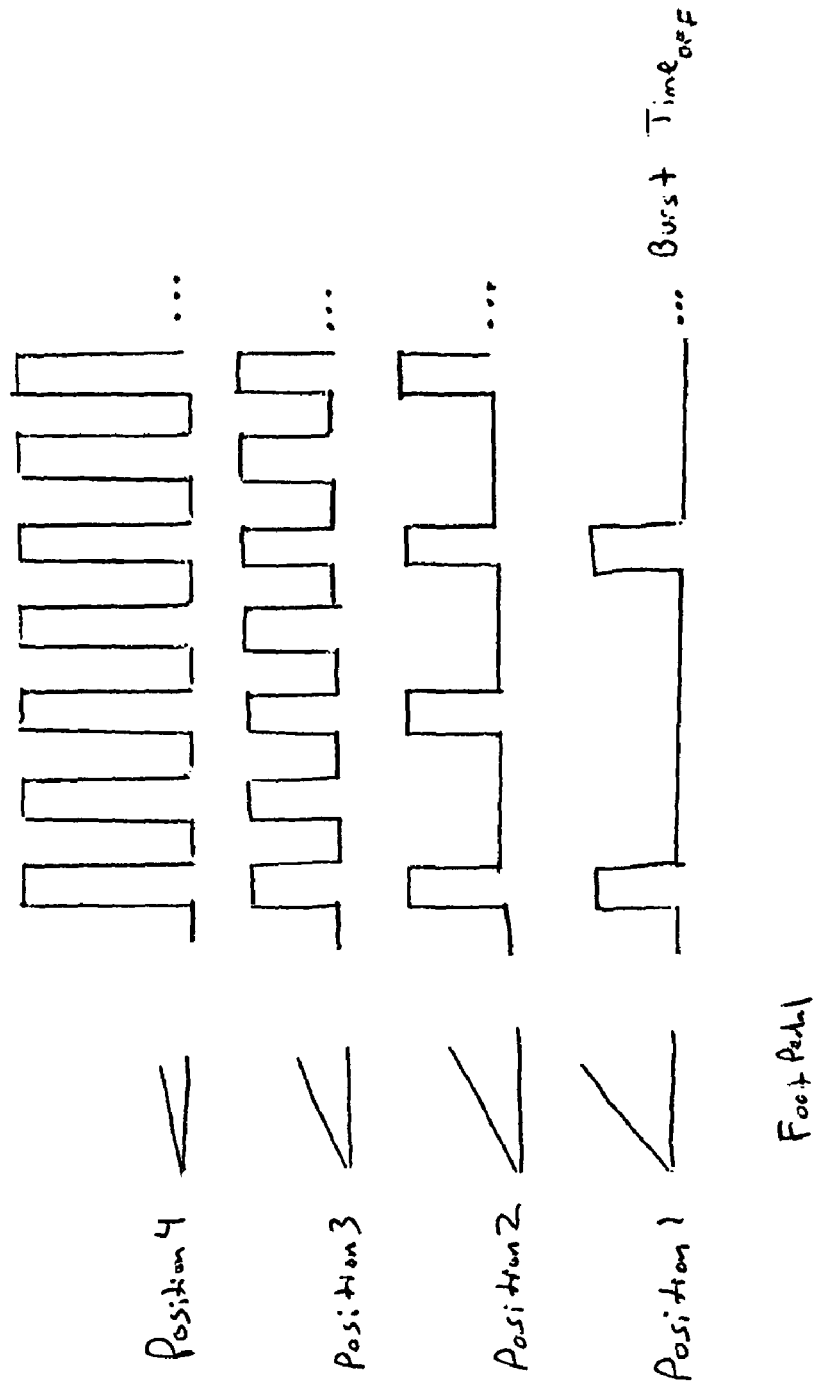
FIG. 19 illustrates continuous transformation of pulse mode pulses to burst mode pulses in response to a controller according to another embodiment.

Referring to FIGS. 18 and 19, alternative embodiments are directed to transforming pulses between burst and pulse modes in response to movement of the foot pedal. FIG. 18 illustrates transitioning from burst mode to pulse mode. The foot pedal is pressed from Position 1 to Position 2 to decrease the off time 1510. The off-time decreases further when the foot pedal is pressed from Position 2 to Position 3. The number of fixed width, constant amplitude pulses in a period of time increases as the foot pedal is pressed further. As the foot pedal is pressed further, the off time 1510 eventually reaches a pre-determined value, such as the on time 1520 or another suitable value. In the illustrated embodiment, the pre-determined value is equal to the on-time 1520. The pulse amplitude is then adjusted after the off time 1510 is the same as the on time 1520 (or another suitable value), thereby increasing energy generated by the handpiece, and transforming pulses from burst mode to pulse mode pulses.

Referring to FIG. 19, in an alternative embodiment, pulses are transformed from pulse mode to burst mode pulses. If the system is initially in pulse mode and the foot pedal is pressed to position 4, releasing the foot pedal initially decreases the amplitude of the pulses. After the amplitude reaches a predetermined amplitude, releasing the foot pedal further results in adjusting the burst mode and increasing the power "Off" time 1510, thereby providing fewer fixed width pulses 1500 in a given time and less power to the ultrasonic tip 113, in order to cool the tip 113.

As shown in FIGS. 18 and 19, a surgeon can advantageously switch between burst mode and pulse mode pulses by manipulating a single controller, e.g., by pressing and releasing the foot pedal. This arrangement is particularly beneficial since these transformations can be achieved without the interruptions and adjustments that are otherwise associated with changing to different pulse modes, e.g., adjusting parameters on a display screen or interface. Instead, embodiments advantageously allow continuous pulse transitions by pressing and releasing the foot pedal as part of a natural and continuous motion of the surgeon's foot, thereby simplifying the configuration and operation of surgical equipment and simplifying surgical procedures.

Figure 20:
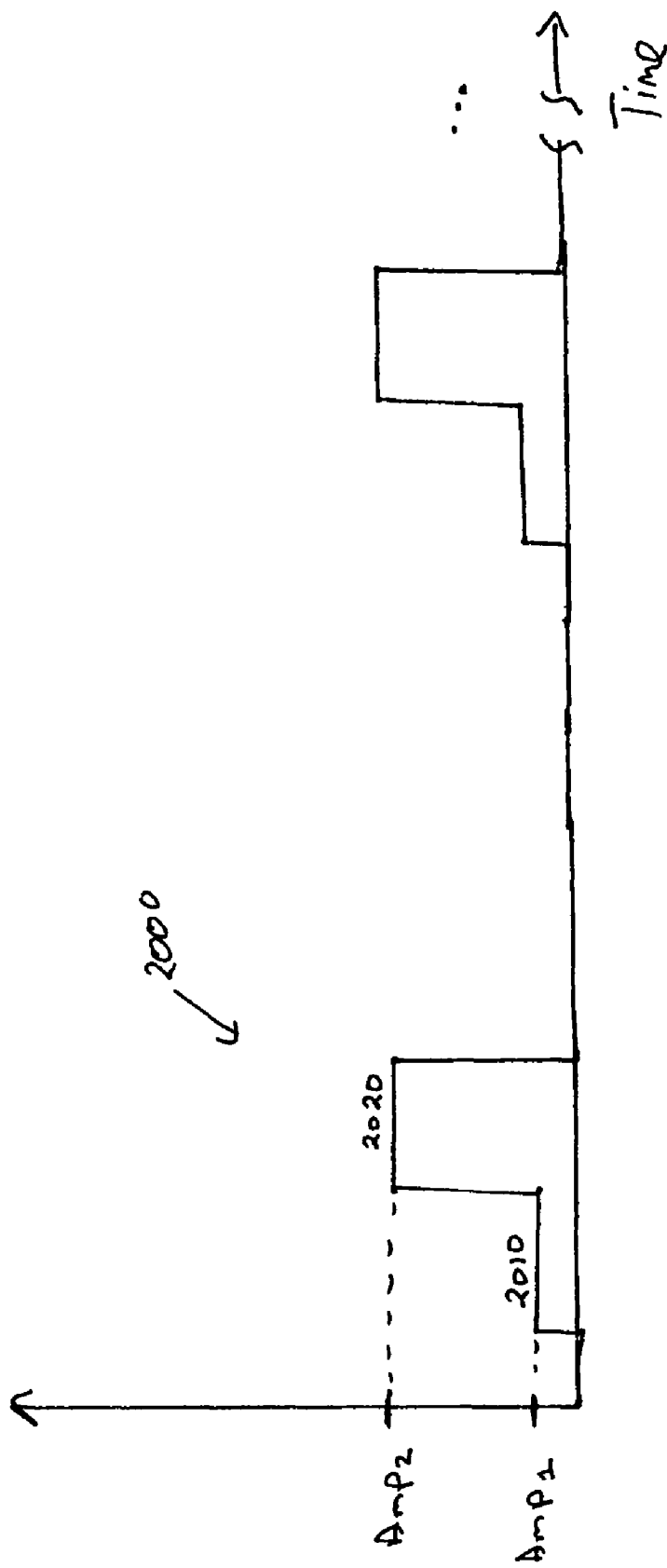
FIG. 20 illustrates multi-segment rectangular pulses having two pulse segments with increasing amplitude according to yet another embodiment.
Figure 21:
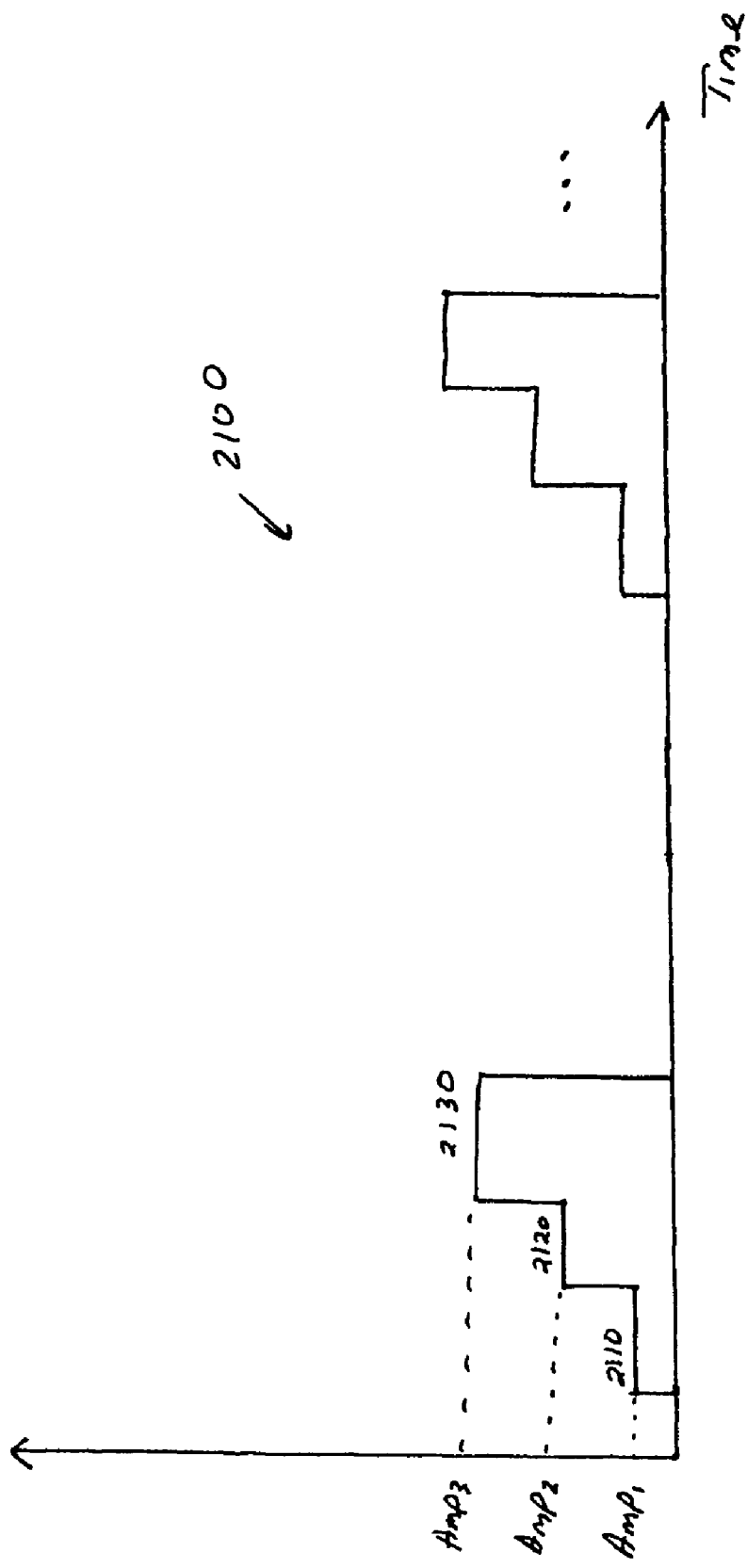
FIG. 21 illustrates a multi-segment rectangular pulse according to an alternative embodiment having three pulse segments with increasing amplitude.

Referring to FIG. 20, in a further alternative embodiment, the amount of power of each pulse can be gradually increased by utilizing a multi-step or multi-segment pulse 2000. Persons skilled in the art will appreciate that a multi-segment pulse can have two, three, four and other numbers of segments. Thus, the two-segment pulse shown in FIG. 20 is provided for purposes of illustration, not limitation.

In the illustrated embodiment, a first step 2010 has less power than a subsequent step 2020. For example, as shown in FIG. 20, a first pulse segment 2010 is at a first amplitude for a predetermined time, followed by a second pulse segment 2020 at a second amplitude for a predetermined time. Configuring a multi-segment pulse to provide a gradual transition from low power to higher power provides the ability to hold and emulsify lens material more accurately in contrast to abrupt transitions from low to maximum power levels such as in a typical square, which can inadvertently move lens material away from the tip during cutting of the lens material Referring to FIG. 21, in alternative embodiments, a multi-segment pulse 2100 may have more than two segments of increasing amplitude. In the illustrated embodiment, a pulse has three pulse segments 2110, 2120 and 2130. Other pulses may have four, five and other numbers of pulse segments as needed.

The different pulses and pulse patterns described above are pulses of ultrasonic energy that can be delivered in packets to transducer elements of the handpiece. For example, as shown in FIGS. 2B and 2C, ultrasonic energy is delivered to piezoelectric elements as intermittent packets of pulses that are separated by an off period. The pulses patterns according to alternative embodiments of the invention described above are delivered to piezoelectric elements of an ultrasound handpiece during these "on" times and within these packets.

For example, FIG. 23 illustrates packets of pulses of ultrasonic energy having sequentially increasing power, as shown in FIG. 10. As a further example, FIG. 24 illustrates packets of pulses of ultrasonic energy having sequentially decreasing power, as shown in FIG. 13. Persons skilled in the art will appreciate that a packet may have one or multiple groups of pulses, and that a packet may end at the end of a group of pulses or in the middle of a group of pulses. For example, FIGS. 22 and 23 illustrate a packet ending with the second pulse in a group of pulses. The packet may also end with the last pulse in the group of pulses. Accordingly, FIGS. 22 and 23 are provided for purposes of illustration, not limitation. Persons skilled in the art will also appreciate that the embodiments of pulses described in this specification are not required to be framed or organized in packets in order to control the ultrasound handpiece.

Although references have been made in the foregoing description to various embodiments, persons of skill in the art will recognize that insubstantial modifications, alterations, and substitutions can be made to the described embodiments without departing from the scope of embodiments.

What is claimed:

1. A method of generating energy for use with an ophthalmic surgical device, the ophthalmic surgical device having a handpiece for generating pulses of energy, the method comprising:
   generating a group of pulses having
      at least one triangular pulse that includes a first programmed substantially linear rise component and a second programmed substantially linear decay component, and
      at least one pulse having an attribute that is different from the triangular pulse.

2. The method of claim 1, wherein generating the group of pulses comprises generating pulses having sequentially different power.

3. The method of claim 2, wherein generating the group of pulses comprises generating pulses having sequentially decreasing power.

4. The method of claim 2, wherein generating the group of pulses comprises generating pulses having sequentially increasing power.

5. The method of claim 1, wherein generating the group of pulses comprises generating pulses having different amplitudes.

6. The method of claim 1, wherein generating the group of pulses comprises generating pulses having the same amplitude.

7. The method of claim 1, wherein generating the group of pulses comprises generating pulses having different on-times.

8. The method of claim 1, wherein generating the group of pulses comprises generating pulses having different shapes.

9. The method of claim 1, wherein generating the group of pulses comprises generating pulses having the same shape.

10. The method of claim 1, wherein generating the group of pulses comprises generating a group of about two to ten pulses.

11. The method of claim 1, further comprising changing the amplitude of the pulses in response to a controller.

12. The method of claim 11, wherein the controller is a foot pedal and changing the amplitude comprises changing the amplitude of the pulses in response to movement of the foot pedal.

13. A method of generating energy for use with an ophthalmic surgical device, the ophthalmic surgical device having a handpiece for generating pulses of energy, the method comprising:
   generating a group of pulses having
      at least one triangular pulse that includes a first programmed substantially linear rise component and a second programmed substantially linear decay component; and
      at least one pulse that does not include a programmed substantially linear component,
      wherein each pulse differs from at least one other pulse in at least one manner.

14. The method of claim 13, wherein generating the group of pulses comprises generating pulses having sequentially different power.

15. The method of claim 14, wherein generating the group of pulses comprises generating pulses having sequentially decreasing power.

16. The method of claim 14, wherein generating the group of pulses comprises generating pulses having sequentially increasing power.

17. The method of claim 14, wherein generating the group of pulses comprises generating pulses having different amplitudes.

18. The method of claim 14, wherein generating the group of pulses comprises generating pulses having the same amplitude.

19. The method of claim 14, wherein generating the group of pulses comprises generating pulses having different on-times.

20. The method of claim 14, wherein generating the group of pulses comprises generating pulses having different shapes.

21. The method of claim 14, wherein generating the group of pulses comprises generating a group of about two to ten pulses.

22. The method of claim 14, further comprising changing the amplitude of the pulses in response to a controller.

23. The method of claim 22, wherein the controller is a foot pedal and changing the amplitude comprises changing the amplitude of the pulses in response to movement of the foot pedal.

* * * * *